United States Patent
Kletter et al.

(10) Patent No.: US 9,528,925 B2
(45) Date of Patent: Dec. 27, 2016

(54) SPATIAL MODULATION OF LIGHT TO DETERMINE OBJECT POSITION

(71) Applicant: Palo Alto Research Center Incorporated, Palo Alto, CA (US)

(72) Inventors: Doron Kletter, San Mateo, CA (US); Joerg Martini, San Francisco, CA (US); Marshall W. Bern, San Carlos, CA (US); Noble M. Johnson, Menlo Park, CA (US); Peter Kiesel, Palo Alto, CA (US); Bowen Cheng, Atherton, CA (US); Michael I. Recht, Mountain View, CA (US)

(73) Assignee: PALO ALTO RESEARCH CENTER INCORPORATED, Palo Alto, CA (US)

(*) Notice: Subject to any disclaimer, the term of this patent is extended or adjusted under 35 U.S.C. 154(b) by 325 days.

(21) Appl. No.: 14/181,560

(22) Filed: Feb. 14, 2014

(65) Prior Publication Data
US 2015/0276387 A1    Oct. 1, 2015

(51) Int. Cl.
| | |
|---|---|
| G01B 11/22 | (2006.01) |
| G01N 15/14 | (2006.01) |
| G01N 21/85 | (2006.01) |
| G01N 15/00 | (2006.01) |
| G01N 15/10 | (2006.01) |

(52) U.S. Cl.
CPC ...... *G01N 15/1459* (2013.01); *G01N 15/1429* (2013.01); *G01N 2015/0038* (2013.01); *G01N 2015/0053* (2013.01); *G01N 2015/1006* (2013.01); *G01N 2021/8592* (2013.01)

(58) Field of Classification Search
CPC ............ G01N 15/1429; G01N 15/1459; G01N 2015/8592; G01N 2015/0038; G01N 2015/0053; G01N 2015/1006; G01B 11/22; G01B 11/046; G01B 11/0691
See application file for complete search history.

(56) References Cited

U.S. PATENT DOCUMENTS

| 4,037,965 A | 7/1977 | Weiss |
| 4,172,227 A | 10/1979 | Tyrer et al. |
| 4,441,816 A | 4/1984 | Hencken et al. |
| (Continued) | | |

FOREIGN PATENT DOCUMENTS

| EP | 1950552 | 7/2008 |
| WO | WO0194938 | 12/2001 |
| WO | WO2005017969 | 2/2005 |

OTHER PUBLICATIONS

File History for U.S. Appl. No. 14/246,912.

(Continued)

*Primary Examiner* — John Lee
(74) *Attorney, Agent, or Firm* — Hollingsworth Davis, LLC

(57) ABSTRACT

Approaches for determining object position in a flow path are disclosed. A system includes a spatial filter having a length disposed along a longitudinal axis of the flow path and a width along a lateral axis of the flow path. The spatial filter has mask features configured to modulate light. Light emanating from objects moving along the flow path is detected. The detected light has a component along a detection axis that makes a non-zero angle with respect to the longitudinal and lateral axes. An electrical output signal that includes information about the trajectory depth of the object is generated in response to the detected light.

27 Claims, 31 Drawing Sheets

(56) References Cited

U.S. PATENT DOCUMENTS

| | | | |
|---|---|---|---|
| 5,682,038 A * | 10/1997 | Hoffman | G01N 15/14 250/226 |
| 6,213,579 B1 | 4/2001 | Cornell et al. | |
| 6,649,416 B1 * | 11/2003 | Kauer | G01N 21/6428 422/82.06 |
| 6,654,521 B2 * | 11/2003 | Sheng | G02B 6/02138 385/37 |
| 7,104,634 B2 | 9/2006 | Weksler et al. | |
| 7,291,824 B2 * | 11/2007 | Kiesel | G01J 1/4228 250/208.2 |
| 7,358,476 B2 | 4/2008 | Kiesel et al. | |
| 7,386,199 B2 | 6/2008 | Schmidt et al. | |
| 7,420,677 B2 | 9/2008 | Schmidt et al. | |
| 7,471,393 B2 * | 12/2008 | Trainer | G01N 15/0205 356/336 |
| 7,471,399 B2 * | 12/2008 | Kiesel | G01N 21/031 356/519 |
| 7,479,625 B2 * | 1/2009 | Kiesel | G01N 21/05 250/226 |
| 7,502,123 B2 * | 3/2009 | Schmidt | G01N 21/253 356/454 |
| 7,547,904 B2 | 6/2009 | Schmidt et al. | |
| 7,688,427 B2 | 3/2010 | Cox et al. | |
| 7,701,580 B2 * | 4/2010 | Bassler | G01N 21/05 356/419 |
| 7,763,856 B2 * | 7/2010 | Kiesel | G01N 21/645 250/343 |
| 7,817,254 B2 * | 10/2010 | Hegyi | G01N 15/12 356/28 |
| 7,817,276 B2 | 10/2010 | Kiesel et al. | |
| 7,894,068 B2 * | 2/2011 | Bassler | G01N 21/645 356/410 |
| 7,961,326 B2 * | 6/2011 | Martini | A61B 5/14532 356/39 |
| 8,153,949 B2 * | 4/2012 | Kiesel | G01N 15/1056 250/208.2 |
| 8,153,950 B2 * | 4/2012 | Kiesel | G01J 3/02 250/208.2 |
| 8,203,711 B2 | 6/2012 | Shinoda | |
| 8,373,860 B2 | 2/2013 | Kiesel et al. | |
| 8,388,569 B2 | 3/2013 | Uhland et al. | |
| 8,437,582 B2 * | 5/2013 | Kiesel | G01J 3/02 385/12 |
| 8,594,470 B2 * | 11/2013 | Kiesel | G01J 3/02 385/115 |
| 8,629,981 B2 * | 1/2014 | Martini | G01N 21/05 356/28 |
| 9,629,981 | 1/2014 | Martini et al. | |
| 8,723,140 B2 * | 5/2014 | Kiesel | G01N 21/6408 250/458.1 |
| 8,821,799 B2 * | 9/2014 | Bassler | G01N 15/147 422/105 |
| 8,921,277 B2 * | 12/2014 | Kiesel | G01N 21/6452 506/7 |
| 9,029,800 B2 * | 5/2015 | Kiesel | G01J 3/36 250/458.1 |
| 9,074,978 B2 * | 7/2015 | Lo | G01P 5/001 |
| 9,114,606 B1 * | 8/2015 | Ready | B41J 2/0456 |
| 9,134,221 B2 * | 9/2015 | Lo | G01N 15/1459 |
| 9,164,037 B2 * | 10/2015 | Bassler | G01N 21/6408 |
| 9,207,066 B2 * | 12/2015 | Martini | G01B 11/046 |
| 9,261,452 B2 * | 2/2016 | Martini | G01N 15/1436 |
| 2003/0138206 A1 * | 7/2003 | Sheng | G02B 6/02138 385/37 |
| 2003/0203502 A1 | 10/2003 | Zenhausern et al. | |
| 2003/0235924 A1 * | 12/2003 | Adams | B01L 3/502715 436/172 |
| 2004/0067167 A1 * | 4/2004 | Zhang | G01N 15/147 422/82.05 |
| 2004/0226386 A1 | 11/2004 | Gysling et al. | |
| 2007/0076210 A1 * | 4/2007 | Kiesel | G01J 9/0246 356/454 |
| 2007/0145236 A1 * | 6/2007 | Kiesel | G01J 1/4228 250/208.1 |
| 2007/0145249 A1 * | 6/2007 | Kiesel | G01N 21/05 250/221 |
| 2007/0146704 A1 * | 6/2007 | Schmidt | B01L 3/502715 356/338 |
| 2007/0146888 A1 * | 6/2007 | Schmidt | G01J 3/02 359/589 |
| 2007/0147728 A1 * | 6/2007 | Schmidt | B01L 3/502715 385/14 |
| 2008/0181827 A1 * | 7/2008 | Bassler | G01N 15/147 422/119 |
| 2008/0183418 A1 * | 7/2008 | Bassler | G01N 21/6408 702/150 |
| 2008/0186488 A1 * | 8/2008 | Kiesel | G01N 21/39 356/335 |
| 2008/0186492 A1 * | 8/2008 | Kiesel | G01N 21/39 356/433 |
| 2008/0186504 A1 * | 8/2008 | Kiesel | G01N 21/031 356/454 |
| 2008/0197272 A1 * | 8/2008 | Kiesel | G01N 21/05 250/226 |
| 2009/0156917 A1 * | 6/2009 | Martini | A61B 5/14532 600/341 |
| 2009/0190121 A1 * | 7/2009 | Hegyi | G01N 15/12 356/28 |
| 2009/0194705 A1 * | 8/2009 | Kiesel | G01N 21/645 250/458.1 |
| 2009/0195773 A1 * | 8/2009 | Bassler | G01N 21/05 356/73 |
| 2010/0155577 A1 * | 6/2010 | Kiesel | G01N 15/1056 250/208.2 |
| 2010/0201988 A1 * | 8/2010 | Kiesel | G01N 21/05 356/419 |
| 2010/0225913 A1 * | 9/2010 | Trainer | G01N 15/0205 356/338 |
| 2011/0222062 A1 * | 9/2011 | Martini | G01N 21/05 356/417 |
| 2012/0194590 A1 | 8/2012 | Suzuki | |
| 2012/0236291 A1 | 9/2012 | Pittaro et al. | |
| 2013/0016335 A1 | 1/2013 | Lo et al. | |
| 2013/0037726 A1 | 2/2013 | Kiesel et al. | |
| 2013/0037728 A1 | 2/2013 | Kiesel et al. | |
| 2013/0083315 A1 * | 4/2013 | Lo | G01J 3/46 356/73 |
| 2014/0152986 A1 * | 6/2014 | Trainer | G01N 15/0205 356/336 |
| 2014/0192359 A1 * | 7/2014 | Martini | G01N 21/05 356/417 |
| 2014/0370612 A1 * | 12/2014 | Bassler | G01N 15/147 436/94 |
| 2015/0105295 A1 * | 4/2015 | Kiesel | G01N 21/6452 506/9 |
| 2015/0177118 A1 * | 6/2015 | Johnson | G01N 15/1436 435/5 |
| 2015/0177119 A1 * | 6/2015 | Martini | G01N 15/1436 435/5 |
| 2015/0185139 A1 * | 7/2015 | Kiesel | G01N 21/645 356/402 |
| 2015/0233703 A1 * | 8/2015 | Martini | G01B 11/043 356/28 |
| 2015/0233704 A1 * | 8/2015 | Martini | G01B 11/0691 356/635 |
| 2015/0276387 A1 * | 10/2015 | Kletter | G01N 15/1429 250/226 |
| 2015/0276486 A1 * | 10/2015 | Martini | G01N 15/1429 356/416 |
| 2015/0280290 A1 * | 10/2015 | Saha | H01M 10/48 429/50 |
| 2015/0285622 A1 * | 10/2015 | Kiesel | G01B 11/14 604/500 |

OTHER PUBLICATIONS

U.S. Appl. No. 14/181,524, Martini et al.
U.S. Appl. No. 14/181,530, Martini et al.

(56) References Cited

OTHER PUBLICATIONS

U.S. Appl. No. 14/181,571, Martini et al.
Kiesel et al., "Spatially Modulated Fluorescence Emission from Moving Particles", Appl. Phys. Lett. 94, 2009, pp. 041107-1-041107-3.
Kiesel et al., "Spatially Modulated Emission Advances Point-of-Care Diagnostics", Laser Focus World, Nov. 2010, pp. 47-50.
U.S. Appl. No. 14/155,094, filed Jan. 14, 2014, Martini et al.
Petersson et al., "Free Flow Acoustophoresis: Micorfluidic-Based Mode of Particle and Cell Separation", Anal. Chem, 79 (14), 2007, pp. 5117-5123.
Yamada et al., "Pinched flow fractionation: continuous size separation of particles utilizing a laminar flow profile in a pinched microchannel", Anal. Chem. 76 (18), Sep. 2004, pp. 5465-5471. (abstract only).
Yamada et al., "Microfluidic Particle Sorter Employing Flow Splitting and Recombining", Anal. Chem. 78, 2006, pp. 1357-1362.
Ji et al., "Silicon-based microfilters for whole blood cell separation", Biomed Microdevices 10(2), 2008, pp. 251-257. (abstract only).
Schrum et al., "Microchip Flow Cytometry Using Electrokinetic Focusing", Anal. Chem. 71 (19), Oct. 1999, pp. 4173-4177. (abstract only).
Huh et al., "Microfluidics for flow cytometric analysis of cells and particles" Physiol. Meas. 26 (3), Jun. 2005, pp. R73-98. (abstract only).
Fu et al., "Electrokinetically driven micro flow cytometers with integrated fiber optics for on-line cell/particle detection", Analytica Chimica Acta, Vo. 507 (1), Apr. 2004, 163-169. (abstract only).
Lee, Gwo-Bin et al., "Micromachine-based multi-channel flow cytometers for cell/particle counting and sorting", J. Micromech, Microeng. 15 (2005) 447-454. (abstract only)
Lin et al., "Vertical focusing device utilizing dielectrophoretic force and its application on microflow cytometer", Journal of Microelectromechanical Systems, vol. 13, No. 6; Dec. 2004; 10 pages.

Zhu et al., "Dielectrophoretic focusing of particles in a microchannel constriction using DC-biased AC flectric fields", Electrophoresis, vol. 30 (15), Jul. 2009. (abstract only).
Chu et al., "A three-dimensional (3D) particle focusing channel using the positive dielectrophoresis (pDEP) guided by a dielectric structure between two planar electrodes", Lab on a Chip, Issue 5m 2009, pp. 688-691. (abstract only).
Chang et al., Three-dimensional hydrodynamic focusing in two-layer polydimethylsiloxane (PDMS) microchannels, J. Michromech. Microeng 17, 2007, pp. 1479-1486.
Sheng et al., "Digital holographic microscope for measuring three-dimensional particle distributions and motions", Applied Optics, Vo. 45 (16), Jun. 2006, pp. 3893-3901.
Lindken et al., "Stereoscopic micro particle image velocimetry" Experiments in Fluids, 41, 2006, pp. 161-171.
Pereira et al., "Microscale 3D flow mapping with µDDPIV", Experiments in Fluids, vol. 42 (4), Apr. 2007, pp. 589-599. (abstract only).
Cheong et al., "Flow Visualizaiton and Flow Cytometry with Holographic Video Microscopy", Optics Express 17, 2009, pp. 13071-13079.
Lima et al., "Confocal micro-PIV measurements of three dimensional profiles of cell suspension flow in a square microchannel", Measurement Science and Technology, vol. 17, 2006, pp. 797-808.
Pugia et al., "Microfluidic Tool Box as Technology Platform for Hand-Held Diagnostics", Clinical Chemistry, vol. 51 (10), 2005, pp. 1923-1932.
File History for U.S. Appl. No. 13/206,436.
File History for U.S. Appl. No. 12/024,490.
File History for U.S. Appl. No. 12/762,702.
File History for U.S. Appl. No. 13/113,021.
File History for U.S. Appl. No. 14/181,524.
File History for U.S. Appl. No. 14/246,893.
File History for EP App. No. 15153858.4 as retrieved from the EP Electronic File System on Aug. 5, 2016, 117 pages.
File History for U.S. Appl. No. 14/181,571.

* cited by examiner

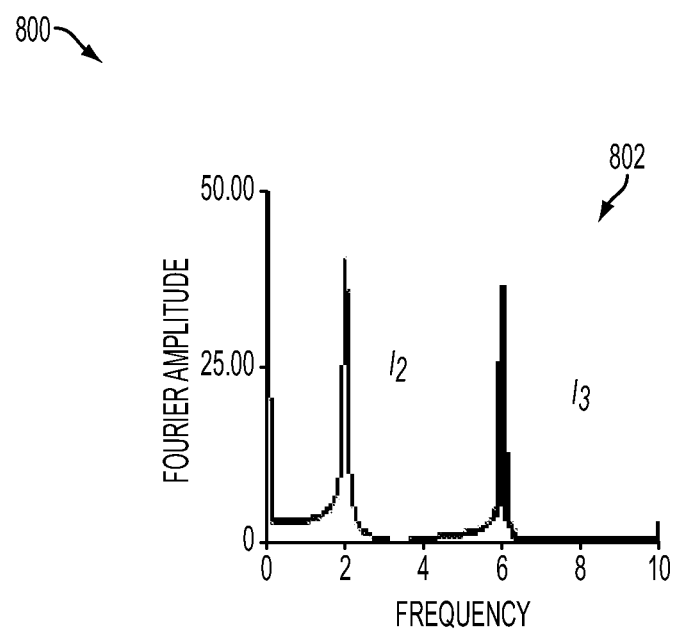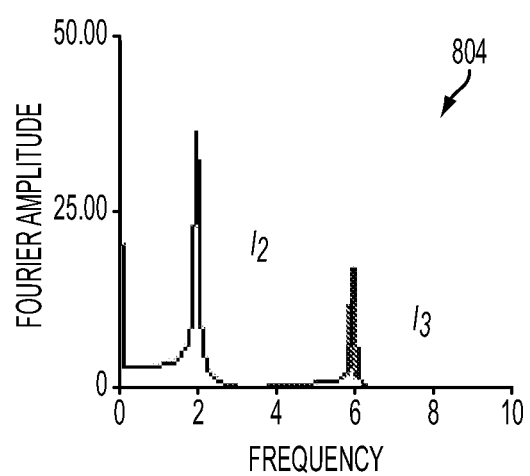
FIG. 6H

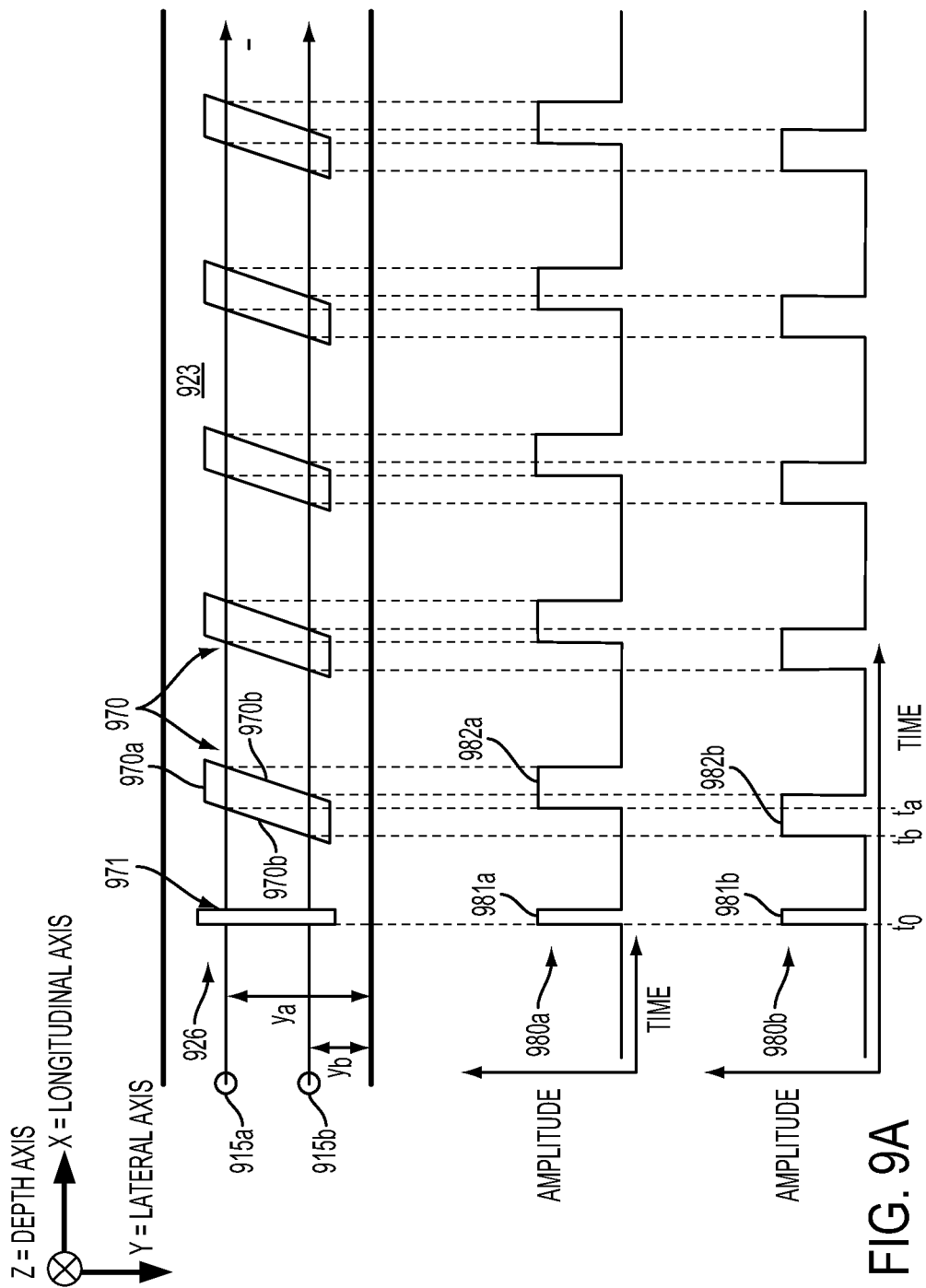

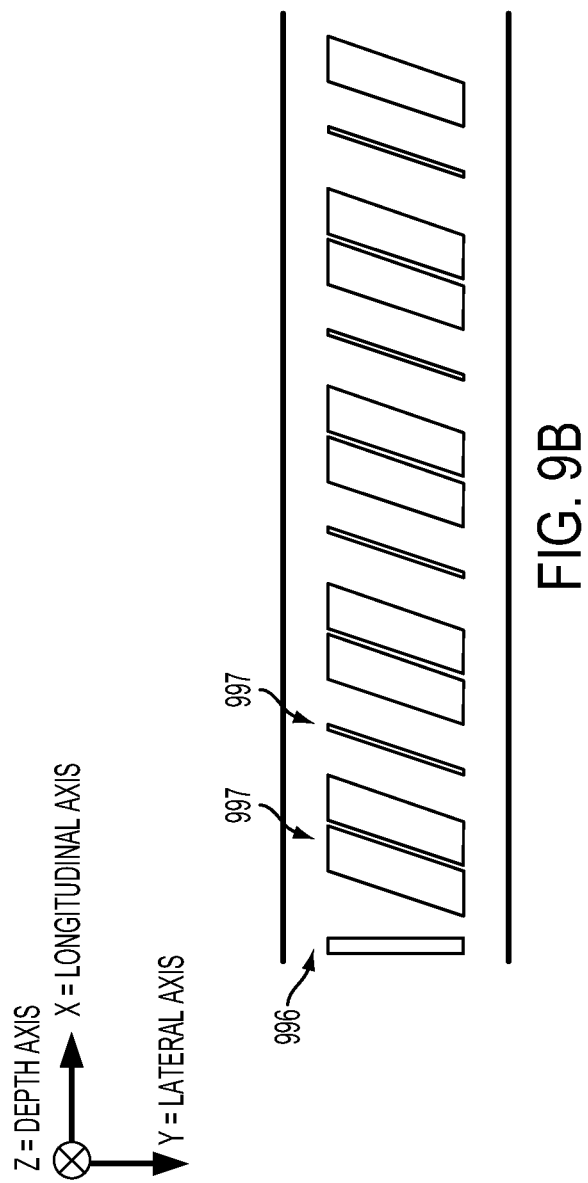

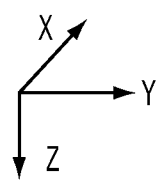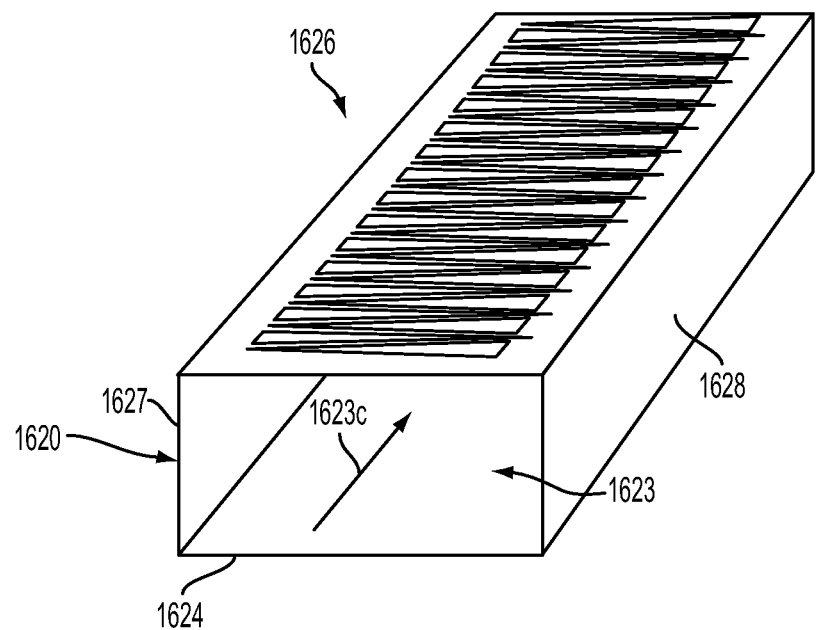
FIG. 14

SPATIAL MODULATION OF LIGHT TO DETERMINE OBJECT POSITION

STATEMENT REGARDING FEDERALLY SPONSORED RESEARCH AND DEVELOPMENT

This invention was made with government support under contract number W911NF-10-1-0479 (3711), awarded by the Department of Defense. The U.S. Government has certain rights in this invention.

TECHNICAL FIELD

This application relates generally to techniques for performing sample analysis by evaluating light emanating from the objects in a sample. The application also relates to components, devices, systems, and methods pertaining to such techniques.

BACKGROUND

The present disclosure relates generally to techniques that determine object characteristics using light emanating from the objects. More specifically, the techniques can use spatial filter and/or mask arrangements to allow for the transmission, reflection, fluorescence, phosphorescence, photoluminescence, chemoluminescence and/or scattering of light with time variation, such as where the objects are moving relative to the spatial filter and/or mask arrangements.

Various techniques have been proposed for using light emanating from objects. For example, U.S. Pat. No. 7,358,476 (Kiesel et al.) describes a fluidic structure with a channel along which is a series of sensing components to obtain information about objects traveling within the channel, such as droplets, cells, viruses, microorganisms, microparticles, nanoparticles, or other objects carried by fluid. A sensing component includes a set of cells that photosense a range of photon energies that emanate from objects. A processor can receive information about objects from the sensing components and use it to obtain spectral information. Additional techniques are described, for example, in U.S. Patent Application Publications 2008/0181827 (Bassler et al.) and 2008/0183418 (Bassler et al.) and in U.S. Pat. No. 7,701,580 (Bassler et al.), U.S. Pat. No. 7,894,068 (Bassler et al.), U.S. Pat. No. 7,547,904 (Schmidt et al.), U.S. Pat. No. 8,373,860 (Kiesel et al.), U.S. Pat. No. 7,420,677 (Schmidt et al.), and U.S. Pat. No. 7,386,199 (Schmidt et al.).

SUMMARY

An assembly includes at least one spatial filter having a length along a longitudinal axis of a flow path and a width along a lateral axis of the flow path. The spatial filter has mask features disposed at least partially along the length of the spatial filter and extending at least partially across the width of the spatial filter. The mask features include at least first mask features having a first optical transmission characteristic and second mask features having a second transmission characteristic different from the first transmission characteristic. At least one detector is positioned to detect light with respect to a detection axis, where the detection axis makes a non-zero angle with respect to the longitudinal and lateral axes, in order to determine the trajectory of the object in the flow path. The detected light is light emanating from at least one object and time modulated according to the mask features as the object moves along the longitudinal axis. The detector is configured to generate a time-varying electrical signal in response to the detected light that includes information about the depth of the object in the flow path. The system also includes an analyzer configured to determine a trajectory depth in the flow path of the object along the detection axis based on the detector signal.

Another embodiment involves a system that determines object position in three dimensional space. A first spatial filter is arranged in an x-y plane of a flow path in three dimensional space characterized by x, y, and z axes, the first mask having a first group of mask features. A second spatial filter is arranged in an x-z plane of the space, the second mask having a second group of mask features. A first detector is positioned to detect light emanating from at least one object and time modulated according to the first group of mask features as the object moves along the flow path. The first detector generates a first time-varying electrical signal in response to the detected light modulated according to the first group of mask features. A second detector is positioned to detect light emanating from at least one object and time modulated according to the second group of mask features as the object moves along the flow path, the second detector configured to generate a second time-varying electrical signal in response to the detected light modulated according to the first group of mask features. An analyzer is configured to determine positions of the object along the x, y, and z axes based on the first and second signals.

Some embodiments involve a method for determining object position in a flow path using a spatial filter having a length disposed along a longitudinal axis of the flow path and a width along a lateral axis of the flow path. The spatial filter has mask features configured to time modulate light. Light emanating from objects moving along the flow path is detected. The detected light has a component along a detection axis that makes a non-zero angle with respect to the longitudinal and lateral axes. An electrical output signal is generated in response to the detected light. A trajectory depth in the flow path of the object along the detection axis is determined based on the output signal.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings wherein:

FIG. 6H illustrates plots of the Fourier amplitudes of the electrical signals from FIG. 6G converted to the frequency domain;

FIG. 9A is a plan view of another spatial filter disposed in the x-y plane and having mask features patterned according to another example embodiment to allow for determination of a lateral position and depth position of an object within the flow path;

FIG. 9B is a plan view of another spatial filter disposed in the x-y plane and having mask features patterned according to another example embodiment to allow for determination of a lateral position and depth position of an object within the flow path;

FIG. 14 is a perspective view of another spatial filter disposed in the x-y plane and having mask features patterned as interdigitated transmissive triangles according to yet another example embodiment to allow for determination of a lateral position of an object within the flow channel;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
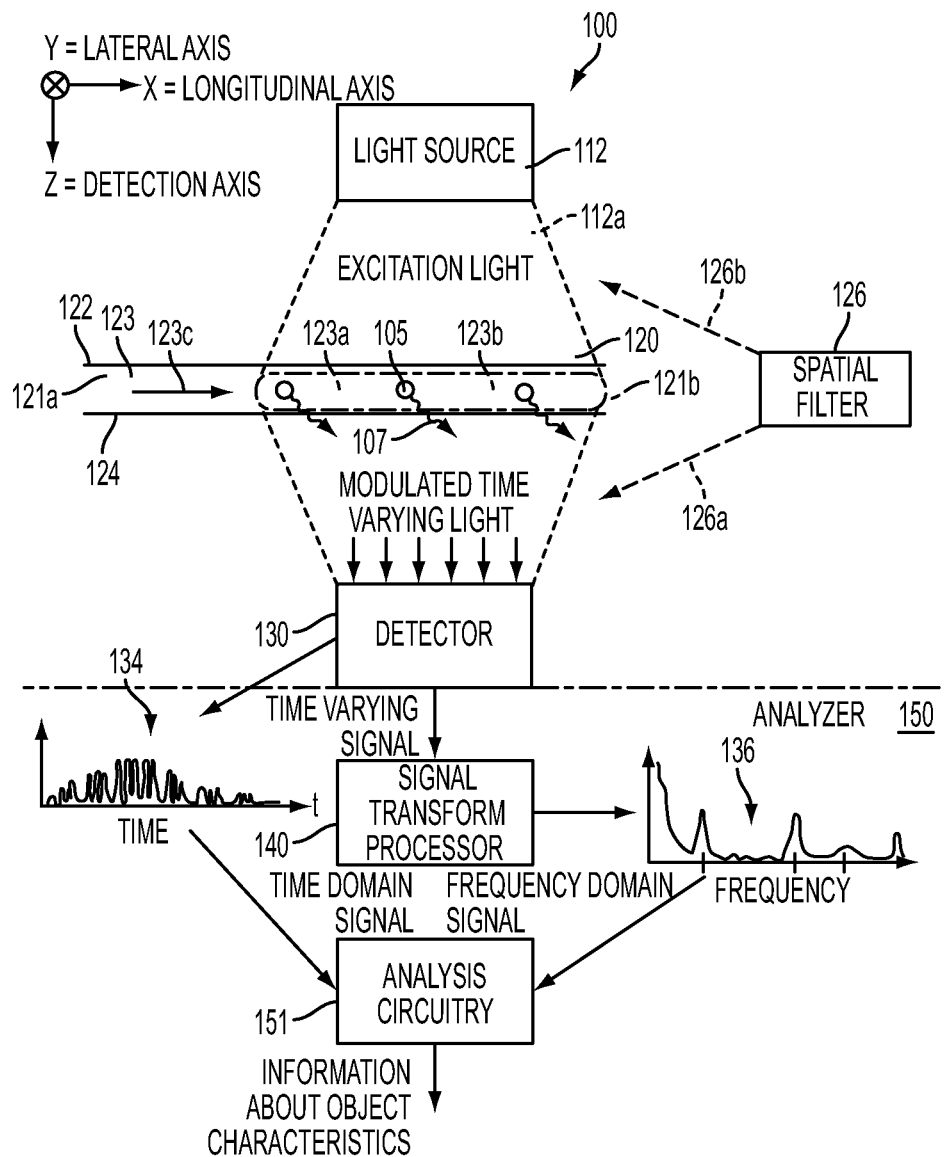
FIG. 1 is an example embodiment of an assembly with a spatial filter, detector, and analyzer configured to determine object characteristics based on spatially modulated light.

Various techniques have been proposed for using light emanating from objects. These techniques have been functionalized for various applications and are generally effective for recognizing and obtaining object characteristics such as size, charge, porosity, surface characteristics, elasticity, and material composition for particular analytes. Light emanating from an object can originate from a multitude of physical processes include: Fluorescence, scattering, up-conversion, second harmonic generation, multi-photon excited fluorescence, Raman scattering, phosphorescence, absorption etc.

The embodiments described herein can be used to perform a position and/or movement analysis of an object. The approaches described herein can be used to determine the object velocity, object position, depth in the flow channel, and/or object trajectory, e.g., three dimensional position and/or trajectory, of moving objects. In some cases, the sizes of the objects is known a priori or can be discerned by the system, and the system may be calibrated to provide an absolute measurement of the object position, velocity and depth trajectory in the flow path, that is, the precise location of the object in the flow channel, at any given time, and over time. In other cases, where the sizes of the objects are unknown, the system may provide a relative depth between objects traveling along the flow path.

The determination of object position and/or trajectory is based on spatially modulated light emanating from the object. The embodiments described herein involve techniques for determining depth along a detection axis, multi-dimensional position and/or trajectory of objects in one or more dimensions as the objects travel along a flow path. Thus, the techniques disclosed can be used to determine a depth position of the object and/or a depth trajectory referenced to a detection axis, a lateral position of the object and/or a lateral trajectory referenced to a lateral axis, and/or a longitudinal position of the object referenced to a longitudinal axis. Determining the trajectory of the object as the object travels in time along the flow channel can include determining directional vectors of travel in one or more dimension. The trajectory can be obtained by sampling the object position over time and determining trajectory vectors based on the multiple position measurements. Object velocity and/or other object characteristics can also be obtained.

The embodiments described herein involve the use of at least one spatial mask that can be deployed in a variety of applications, including analysis of system properties and/or detection of various characteristics of an analyte in a sample. As the object moves along a flow direction, the object emanates spatially modulated light that is detected by a detector. The detector generates a time varying output signal in response to the sensed spatially modulated light emanating from the object. In some implementations, a non-imaging or non-pixilated photodetector can be used to generate a time varying electrical output signal based on the spatially modulated light. The use of a non-imaging photodetector, e.g., a non-pixelated detector, may enhance compatibility with high-throughput cytometry. For example, approaches disclosed herein may obtain object characteristics such as position, trajectory, etc., directly with a non-pixelated detector and a suitable spatial mask rather than recording an image sequence for each object, requiring extraction of object information from the images to determine object characteristics.

It will be understood that the techniques, apparatuses, systems, and methods described herein are applicable to detect various objects such as analytes or particles present in a sample. The term "object" refers broadly to any object of interest to be detected. In some applications, objects of interest are particles or analytes that are relatively small, and may be microscopic in size. A given particle or analyte may be or include one or a collection of biological cell(s), virus(es), molecule(s), certain proteins or protein chains, DNA or RNA fragments, sub-molecular complex(es), droplets (e.g. oil in water), gas bubbles, microparticles, nanoparticles, beads or other small particles that can bind and carry specific chemicals or other analytes, emulsions, any such type of object in an array such as an array of sample wells, and a distinguishable region of a surface such as a small area of a sheet of paper or other image-bearing medium; a distinguishable region, could, for example, be a colored spot, or other bit(s) of matter, for example.

In some embodiments, sensors can obtain information about objects by receiving signals from them; for example, signals in the form of light can emanate from an object, whether through emission (e.g. radiation, fluorescence, incandescence, chemoluminescence, bioluminescence, other forms of luminescence, etc.), scattering (e.g. reflection, deflection, diffraction, refraction, etc.), or transmission, and can be sensed by a photodetector. Cells or other particles may be treated, e.g., stained or tagged with a suitable fluorescent probe or other agent, in such a way that they emit light or absorb light in a predictable fashion when illuminated with excitation light. In this regard, the light emitted by a given excited particle may be fluorescent in nature, or it may constitute a form of scattered light such as in the case of elastic or inelastic (Raman scattering) scattered light. For simplicity, the light that emanates from (by e.g., scattering, emission, or transmission) an object is referred to herein as "emanating light" or "light emanating." It will be understood that the techniques, assemblies, apparatuses, systems, and methods described herein are applicable to detecting all forms of light emanating from an object or constituent parts thereof.

In some embodiments, the detector generates at least one time varying signal in response to the spatially modulated light. The time varying signal includes information about the object's movement and position. In some embodiments, the time varying signal can be analyzed in the time domain to extract the movement and position information and/or to obtain other characteristics of the object. For example, the time varying signal may be compared or correlated to a known template signal and/or the time varying signal may be analyzed by examining various morphological characteristics of the time varying signal.

In some embodiments, the time varying signal may be transformed from the time domain to the frequency domain and the analysis may be carried out on the frequency domain signal. For example, in some cases the Fourier transform of the time varying signal or portions of the time varying signal is used to evaluate the signal. A Fourier transform relates a signal to a set of coefficients of sinusoidal base functions. The coefficients are sometimes referred to as the amplitude of the Fourier transform. In some implementations, the absolute value of the coefficients, or other functions of the coefficients, are referred to as the amplitude of the Fourier transform. For finite length signals or functions one practical Fourier transform is the so called fast Fourier transform (FFT).

FIG. 1 is an example of an assembly 100 configured to determine object characteristics based on spatially modulated light. The assembly 100 includes a light source 112, a mask, e.g., a spatial filter 126, a flow path, e.g., fluidic device 120, a detector 130, a signal processor 140, and an analyzer 150. Components of the assembly are arranged in a coordinate system that includes a longitudinal axis, designated as the x-axis herein, a lateral axis, designated as the y-axis, and a depth axis, designated as the z-axis. In the description below, the flow direction of the flow path and/or flow channel is selected to lie along the longitudinal axis of the coordinate system, and the longitudinal, lateral, and depth axes are orthogonal to one another. Those skilled in the art will appreciate that any coordinate system could alternatively be selected, the arrangement of the assembly with respect to the coordinate system is arbitrary and does not change the operation of the assembly, and that non-orthogonal axis systems could alternatively be used.

The device 120 is adapted to receive a sample of interest to be analyzed. The sample may enter the device 120 at an inlet 121a thereof and exit the device 120 at an outlet 121b thereof, flowing generally along the x-direction through a flow channel 123 formed between confining members 122, 124. The members 122, 124 may be or comprise plates or sheets of glass, plastic, or other suitable materials. One or both of members 122, 124 may be a microscope slide or a microscope cover glass, or portion thereof. The members 122, 124 need not, however, be planar in shape. For example, they may be portions of a unitary tube or pipe having a cross section that is circular, rectangular, or another shape. Other non-planar shapes are also contemplated. In some cases, confinement of the sample may not be necessary, whereupon one or both of members 122, 124 may be omitted. At least a portion of the confining member 122 is transmissive to excitation light emitted by the light source 112 at least in an excitation region 123a. In that regard, light source 112 may emit excitation light 112a towards the fluidic device 120.

In some cases, for example, the light source 112 may comprise a laser or laser diode, a conventional light emitting diode (LED) source or a resonant cavity LED (RC-LED) source. If desired, the light source may incorporate one or more filters to narrow or otherwise tailor the spectrum of the resultant output light. Whichever type of light source is selected, the spectral makeup or composition of the excitation light emitted by the source 112 is preferably tailored to excite, scatter, or otherwise cause emanation of light from at least some of the objects that may be present in the sample, as discussed further below.

The sample is depicted as containing objects 105 that emanate light 107 in all directions (only some directions are illustrated). The objects 105 may have a variety of characteristics, some of which can be determined by the analyzer 150 based on the emanating light 107.

The detector 130 receives time varying light and generates an electrical signal in response to the time varying light. The time variation in the light detected by the detector 130 may be the result of interaction between the excitation light and an input spatial filter to create spatially patterned excitation light that illuminates the object 105. Alternatively, the time variation in the light detected by the detector 130 may be the result of interaction between light emanating from the objects 105 and an output spatial filter. In some embodiments, the detector includes an optical filter arranged between the detector and the objects. An optical filter can be particularly useful when the emanating light is fluorescent light and the optical filter is configured to substantially block the wavelengths of the excitation light and to substantially pass the wavelengths of the light emanating from the objects.

The assembly 100 of FIG. 1 includes the spatial filter 126 (sometimes referred to as a mask) which can be positioned in various locations. Dashed arrows 126a and 126b indicate possible locations of the spatial filter 126 to provide spatially modulated light and/or modulated excitation light. In some configurations, indicated by arrow 126a, the spatial filter 126 can be arranged disposed between the flow channel 123 and the detector 130. In this position, the spatial filter 126 is referred to as an output spatial mask. In other configurations, indicated by arrow 126b, the spatial filter 126 can be arranged placed between the light source 112 and the flow channel 123. In this position, the spatial filter 126 is referred to as an input spatial filter. An input spatial filter may be adapted to transmit light emitted by the light source by varying amounts along the excitation region 123a of the flow channel 123. In this configuration, the input spatial filter creates patterned excitation light in the excitation region 123a of the flow channel 123. According to various implementations, an input spatial filter may comprise a physical mask including a sequence or pattern of first regions that have a first optical transmission characteristic, e.g., are more light transmissive, and second regions that have a second optical transmission characteristic, different from the first characteristic, e.g., are less light transmissive. Note that the terms "first" and "second" are used herein to identify different features, groups, characteristics, etc. of various components discussed herein. These terms are used for identification purposes only and are not meant imply any particular order or any particular spatial relationship unless specifically indicated. For example, "first" mask features may be arranged upstream or downstream of "second" mask features along the flow direction.

The input spatial filter may alternatively or additionally comprise micro-optics or a patterned light source configured to create the excitation pattern. The excitation pattern can be imaged and/or directed onto the excitation region 123a using optical components for the imaging (e.g., lenses) and/or direction, (e.g., fiber optics or waveguides).

In some embodiments an output spatial filter may be utilized and arranged disposed between the objects 105 and the detector 130 at a detection region 123b of the flow channel. In some embodiments, the excitation region 123a and the detection region 123b overlap. In other embodiments, there may be partial overlap between the excitation and detection regions or the excitation and detection regions may be non-overlapping or multiple detection regions and/or excitation regions may be used with various overlapping and/or non-overlapping arrangements. In the assembly 100 shown in FIG. 1, the output spatial filter may be adapted to interact with the light 107 emanating from the objects 105 in the flow channel 123. In some embodiments, the output spatial filter may be a physical mask comprising a sequence or pattern of first regions that are more light transmissive and second regions that are less light transmissive. In some embodiments, color spatial filters may be used such that a first region of the color spatial filter is more transmissive to a first wavelength band and less transmissive to a second wavelength band and a second region of the color spatial filter is less transmissive to the first wavelength band and is more transmissive to the second wavelength band.

According to some embodiments of an assembly 100 that include an input spatial filter, as an object 105 travels in the flow direction 123c in the excitation region 123a of the flow channel 123, light emanating from the light source 112 is alternately substantially transmitted to the object 105 and substantially blocked or partially blocked from reaching the object 105 as the object 105 travels along the flow direction 123c. The alternate transmission and non-transmission (or reduced transmission) of the excitation light 112a along the flow direction 123c produces time-varying light 107 emanating from the object 105. The time-varying light 107 emanating from the object 105 falls on the detector 130 and, in response, the detector 130 generates a time-varying detector output signal 134.

According to some embodiments of the assembly 100 that include the output spatial filter configuration, light 112a from the light source 112 illuminates the object 105, causing the object 105 to emanate light 107. As the object 105 travels in the flow direction 123c in the detection region 123b of the flow channel 123, the output spatial filter alternatively entirely or substantially blocks the light 107 emanating from the object 105 from reaching the detector 130 and substantially transmits the light 107 emanating from the object 105 to the detector 130. The alternate substantial transmission and blocking (or partial blocking) of the light 107 emanating from the object 105 as the object 105 flows through the detection region 123b produces time varying light that falls on the detector 130. In response, the detector 130 generates the time-varying detector output signal 134.

In some embodiments such as the embodiment of FIG. 1, the analyzer 150 may include a signal transform processor 140 that converts the time-varying detector output signal 134 to a frequency domain output signal 136 so as to provide spectral power as a function of frequency. The signal transform processor 140 is shown as part of the analyzer 150 in this embodiment, but may be part of the detector in some embodiments or may comprise separate circuitry in other embodiments. For example, in some embodiments, the signal transform processor may be part of the analyzer circuitry along with the detector.

For conversion, the signal processor 140 may use known techniques such as discrete Fourier transform including, for example, a Fast Fourier Transform "FFT" algorithm. Thus, the frequency domain output signal 136 represents the frequency component magnitude of the time-varying detector output signal 134, where the frequency component magnitude is the amount of a given frequency component that is present in the time-varying detector output signal 134 or function. The Fourier signal power is a relevant parameter or measure because it corresponds to the function or value one would obtain by calculating in a straightforward manner the Fourier transform (e.g. using a Fast Fourier Transform "FFT" algorithm) of the time-varying signal 134. However, other methods or techniques of representing the frequency component magnitude, or other measures of the frequency component magnitude, may also be used. Examples may include e.g. the square root of the Fourier signal power, or the signal strength (e.g. as measured in voltage or current) obtained from a filter that receives as input the time-varying detector output signal 134.

In FIG. 1, the time-varying detector output signal 134 and/or the frequency domain detector output signal 136 can be passed to the analysis circuitry 151 of the analyzer 150. The analysis circuitry 151 is configured to receive the time-varying detector output signal 134 and/or the frequency domain detector output signal 136 and to determine one or more spatial characteristics of the object 105 including a trajectory depth within the flow channel 123 of the object 105 based upon the time-varying detector output signal 134 and/or the frequency domain detector output signal 136. As will be discussed subsequently, the various embodiments discussed herein provide examples of techniques for determining the one or more spatial characteristics of the object 105 using various mask designs and processing techniques. As used herein, the trajectory depth within the flow channel 123 of the object 105 is a distance of the object 105 within the flow channel 123 as measured along the z-direction of the Cartesian coordinate system of FIG. 1. Thus, the trajectory depth within the flow channel is a distance generally perpendicular to the flow direction 123c along the flow channel 123. In some embodiments, the depth can be measured relative to a component such as the filter or one of the confining members.

Figure 2A:
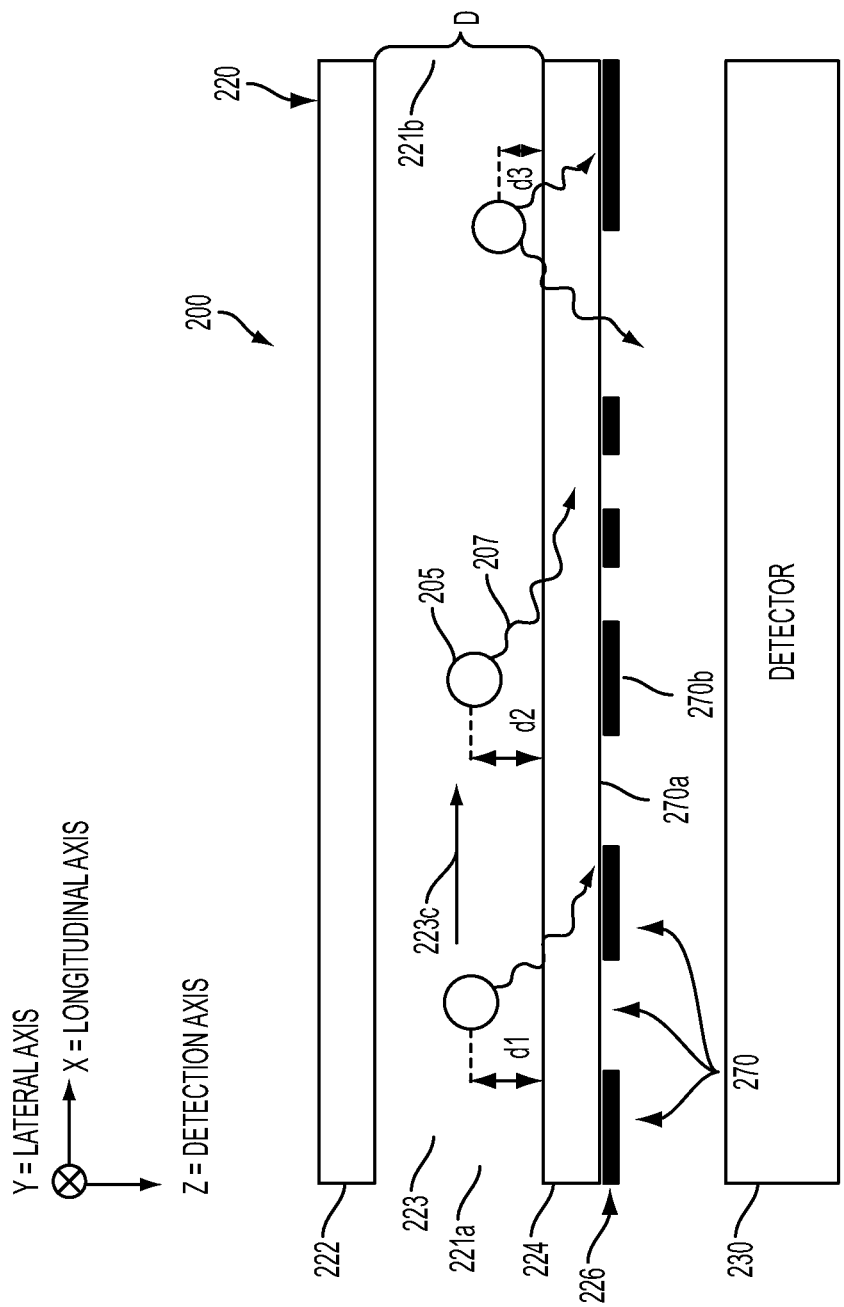
FIG. 2A is a more detailed schematic view of another example embodiment of a fluidic device, spatial filter, and detector.

FIG. 2A and is an enlarged schematic view of a portion of an assembly 200 according to another example embodiment. The portion of the assembly 200 illustrated in FIG. 2A includes a flow path, e.g., fluidic device 220, a detector 230, and a spatial filter 226. The device 220 is adapted to receive a sample of interest to be analyzed. The sample may enter the device 220 at an inlet 221a thereof and exit the device 220 at an outlet 221b thereof, flowing generally in a flow direction 223c along the x-direction through a flow channel 223 formed between confining members 222, 224. As illustrated in FIG. 2A, the one or more objects 205 that comprise the sample can have differing trajectory depths $d_1$, $d_2$, and $d_3$ within the flow channel 223 as measured in the z-direction of the Cartesian coordinate system illustrated. For convenience, depths $d_1$, $d_2$, and $d_3$ are shown as measured relative to confining member 224, however, such is not always the case, and a different reference point for the depth measurement could be used. The objects 205 of the sample may have different positions along the flow channel 223 in the x-direction (generally along the flow direction 223c of the flow channel 223) as well as different lateral positions in the y-direction of the Cartesian coordinate system within the flow channel 223.

As discussed previously, the spatial filter 226 may comprise, for example, a spatial mask. As will be discussed in greater detail subsequently, the spatial filter 226 may have a plurality of mask features 270. The mask features 270 include regions 270a having a first optical transmission characteristic, e.g., more light transmissive regions, and regions 270b having a second optical transmission characteristic, e.g., less light transmissive regions. For simplicity of explanation, many examples provided herein refer to mask features comprising more light transmissive regions and mask features or regions comprising less light transmissive regions. However, it will be appreciated that the optical transmission characteristics of the first and second types of mask features may differ optically in any way, e.g., the first features may comprise regions having a first optical wavelength pass band and the second features may comprise regions having a second optical wavelength pass band different from the first optical wavelength pass band. The pattern or sequence of first features 270a and second features 270b define a transmission function that changes based on a three dimensional position of a light 207 emanating object 205 within the flow channel 223 (i.e., as measured along the x-direction, y-direction, and z-direction of the Cartesian coordinate system). This transmission function may be substantially periodic, or it may instead be substantially non-periodic. The transmission function is sensed by the detector 230, which is configured to output the time-varying output signal discussed in FIG. 1 in response.

In the embodiment of FIG. 2A, the spatial filter 226 may be substantially monochromatic or polychromatic as desired. In a monochromatic mask, the first mask features 270a may be more light transmissive and may all have substantially the same transmission characteristic, and the second mask features 270b may be less transmissive than the first mask features or may be non-transmissive (opaque) and also all have substantially the same transmission characteristic (different from that of the first mask features 270a). In a simple case, the transmissive regions 270a may all be completely clear, as in the case of an aperture, and the less transmissive regions 270b may be completely opaque, as in the case of a layer of black ink or other absorptive, reflective, or scattering material. Alternatively, the transmissive regions 270a may all have a given color or filter characteristic, e.g., high transmission for light emanating from an excited object, but low transmission for excitation light. Alternatively, the less transmissive regions 270b may have a low but non-zero light transmission, as in the case of a grey ink or coating, or a partial absorber or reflector.

In the embodiment of FIG. 2A, the spatial filter 226 is positioned between the objects 205 and the detector 230. In some configurations, the spatial filter 226 may be positioned within the flow channel, such as along the top surface of confining member 224 as shown in FIG. 2A. The light emanating 207 from the objects 205 interacts with the spatial filter 226 to provide time modulation of the sensed light that falls on the detector 230 as the object 205 travels in the flow channel 223. In the illustrated embodiment, the spatial filter 226 is positioned between the objects 205 and the detector 230 without additional optical structures between the spatial filter 226 and the detector 230.

Figure 2B:
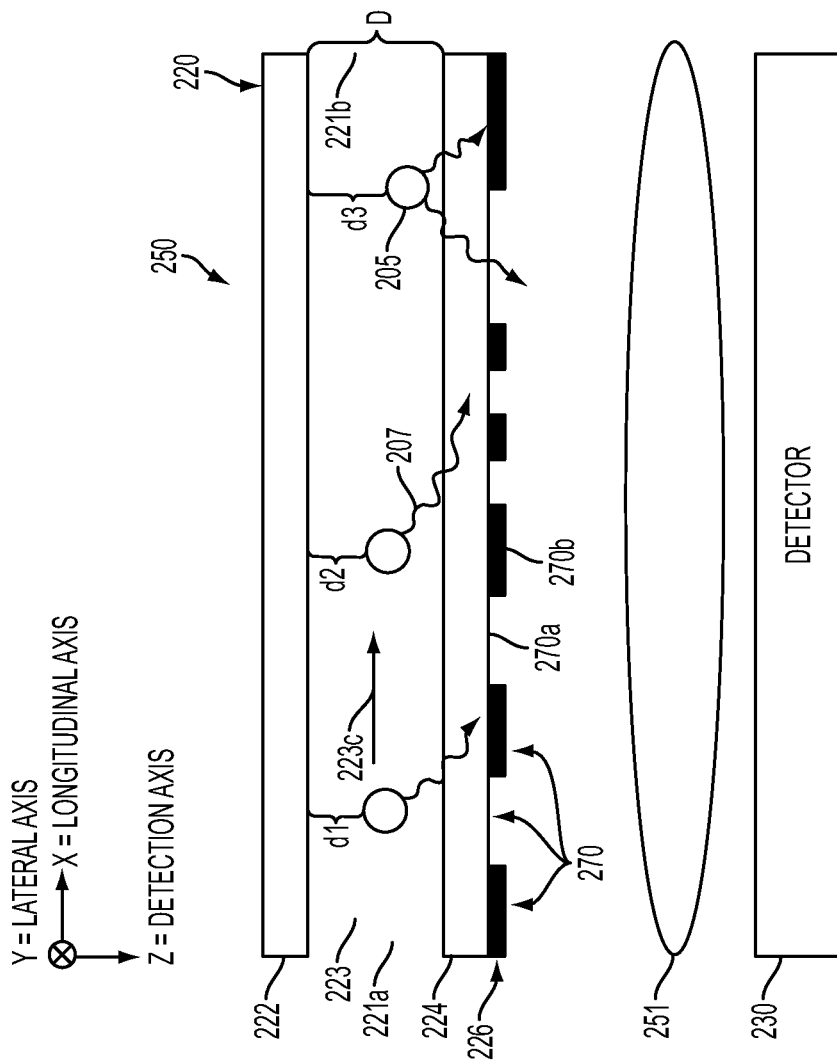
FIG. 2B is a schematic view of yet another example embodiment of fluidic device, spatial filter, and detector with an optical component positioned between the spatial filter and the detector.
Figure 3:
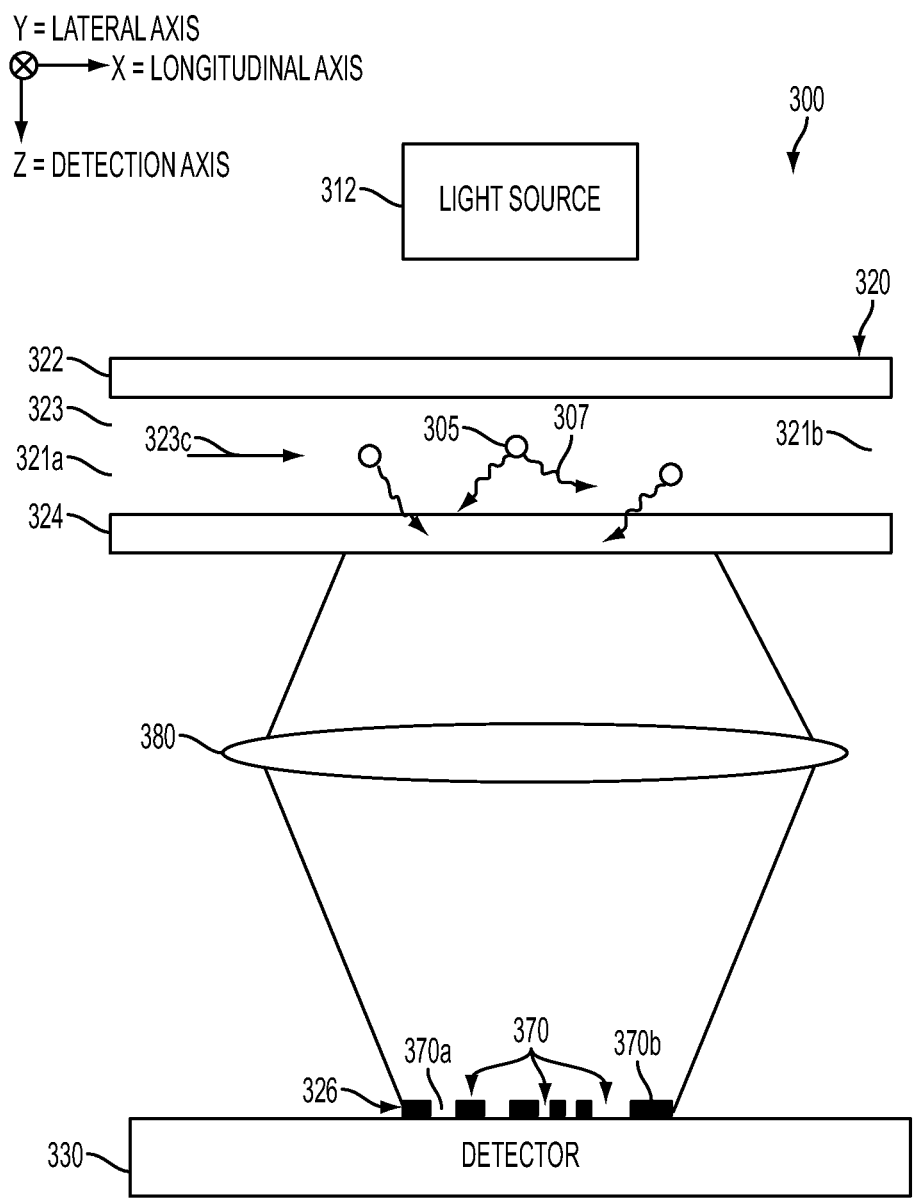
FIG. 3 is a schematic view of another example embodiment of an assembly with an optical imaging element positioned between the object and detector and the spatial filter positioned adjacent the detector.

FIG. 2B is an enlarged schematic view of a portion of an assembly 250 according to another example embodiment. In FIG. 2B, the fluidic device 220, spatial filter 226, and detector 230 may be the same as those depicted in FIG. 2A. The assembly portion 250 shown in FIG. 2B includes an optical element 251 positioned between the spatial filter 226 and the detector 230. The imaging element 251 may be configured to focus the spatially modulated light onto the detector 230, for example FIG. 3 is a schematic view of another embodiment of a portion of an assembly 300 according to another example that includes a remote sensing mask. The portion of the assembly 300 illustrated includes a light source 312, a spatial filter 326, a flow path, e.g., fluidic device 320, and a detector 330. Similar to the embodiments of FIGS. 1, 2A, and 2B, the device 320 includes an inlet 321a, an outlet 321b, a flow channel 323 having a flow direction 323c, and confining members 322, 324. The spatial filter 326 includes mask features 370 with light transmissive regions 370a and less transmissive regions 370b. In FIG. 3, the spatial filter 326 is positioned between the objects 305 and the detector 330 and is positioned remotely from the flow channel 323 immediately adjacent the detector 330. An optical imaging element 380 such as a lens is positioned between the objects 305 and the filter 326 and is configured to image light from the objects 305 onto at least one of the spatial filter 326 and detector 330. The light emanating from the objects 305 and imaged by the element 380 interacts with the spatial filter 326 to provide time modulation of the sensed light received by the detector 330.

Figure 4:
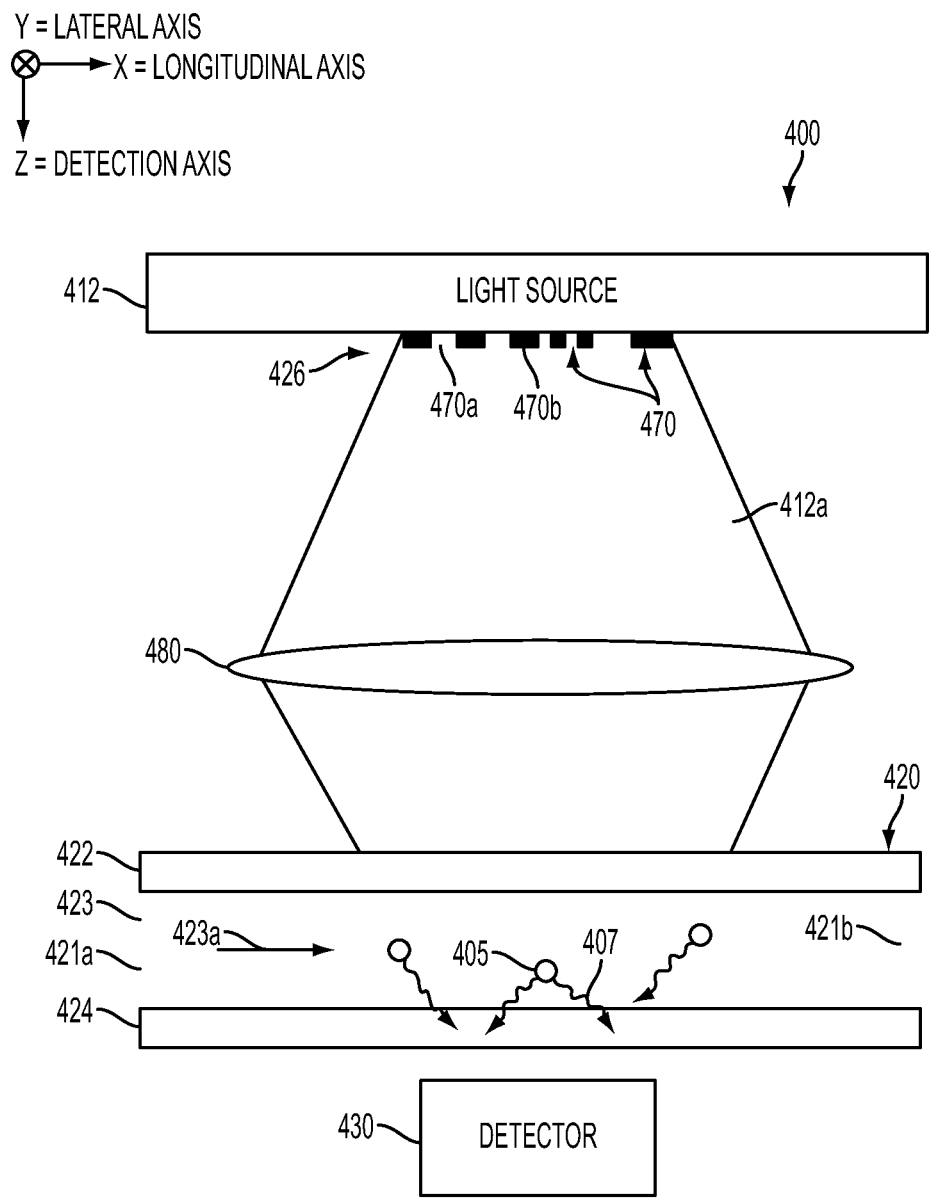
FIG. 4 is a schematic view of another example embodiment of an assembly with the optical imaging element positioned between the light source and the detector and the spatial filter positioned adjacent the light source.

FIG. 4 is a schematic view of yet another embodiment of a portion of an assembly 400. The portion of the assembly 400 illustrated includes a light source 412, a spatial filter 426, a flow path, e.g., fluidic device 420, and a detector 430. Similar to the previously discussed embodiments, the device 420 includes an inlet 421a, an outlet 421b, a flow channel 423 having a flow direction 423a and confining members 422, 424. The spatial filter 426 includes mask features 470 with light transmissive regions 470a and less transmissive regions 470b. In FIG. 4, the spatial filter 426 is positioned between the light source 412 and the fluidic device 420 containing the objects 405. As shown, the spatial filter 426 is positioned remotely from the flow channel 423 immediately adjacent the light source 412. Interaction between the output light from the light source 412 and the spatial filter 426 causes spatially modulated excitation light 412a. An optical imaging element 480 is positioned between the filter 426 and the objects 405 and is configured to image the spatially modulated excitation light 412a onto an excitation region of the flow channel 423. Additionally, the optical imaging element 480 may incorporate one or more filters to narrow or otherwise tailor the spectrum of the resultant spatially modulated excitation light. The spatially modulated excitation light causes light 407 emanating from the objects 405 to be spatially modulated as well. The spatially modulated light emanating from the objects 405 is sensed by the detector 430.

Figure 5A:
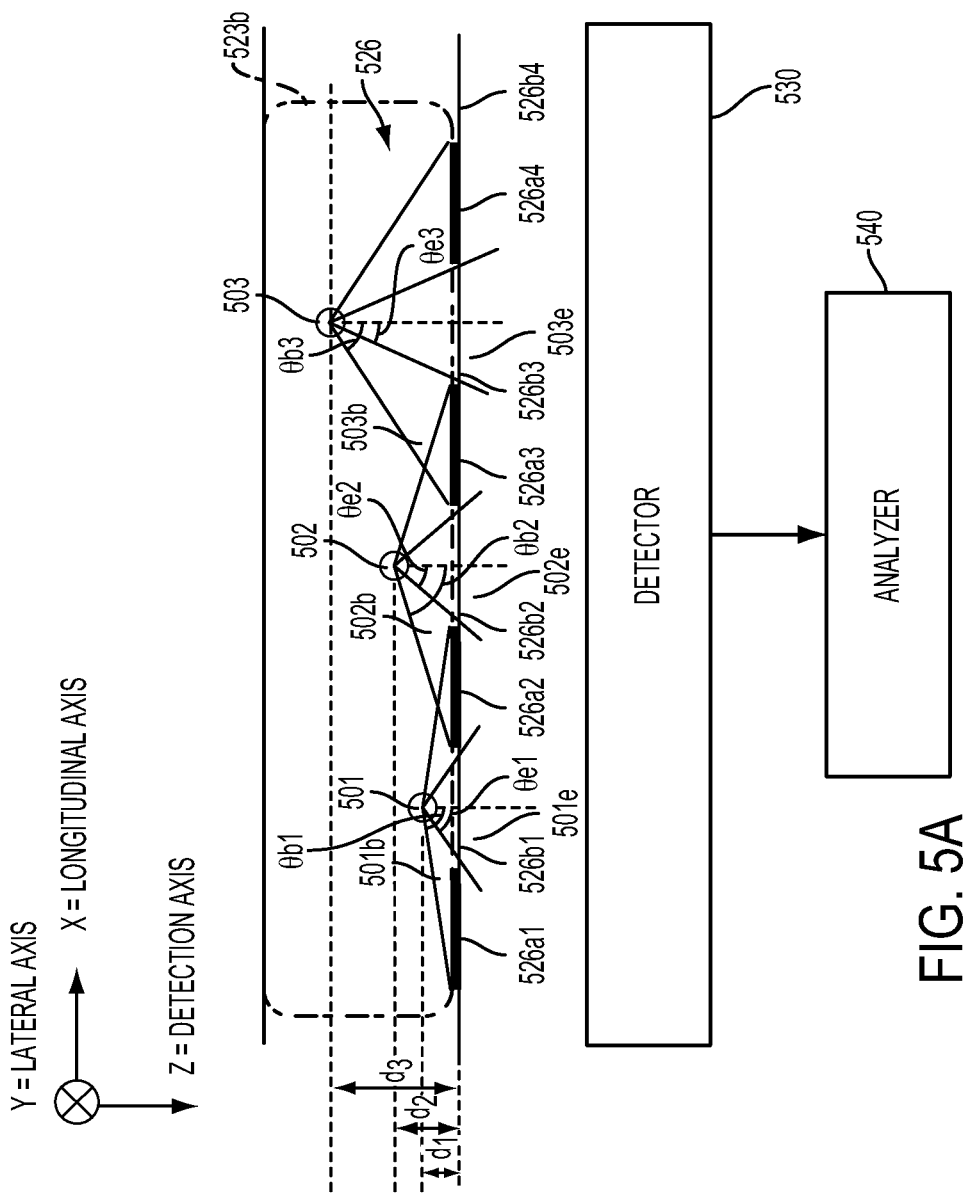
FIGS. 5A through 5I illustrate approaches for determining depth of objects moving in a flow path in accordance with various embodiments

FIGS. 5A through 5H illustrate approaches for determining trajectory depth of objects moving in a flow path in accordance with various embodiments. FIG. 5A is a side view of a portion of an assembly 500 including spatial filter 526 arranged in a three dimensional space referenced to a coordinate system of lateral, longitudinal, and depth axes. The axes x, y, z used for reference in the illustrated embodiment are orthogonal, but non-orthogonal coordinate axes could alternatively be used.

Figure 5B:
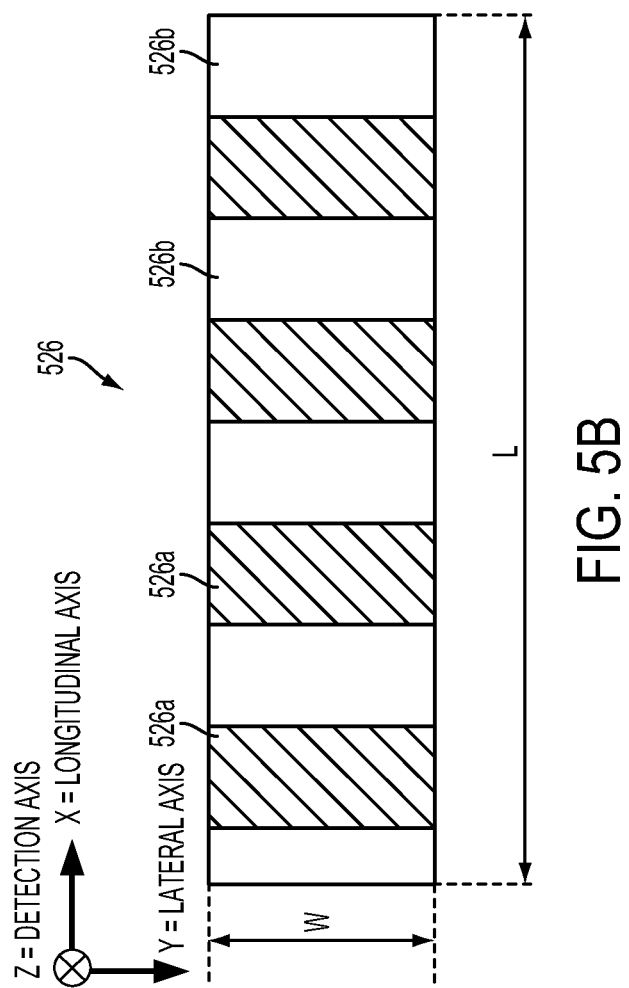

FIG. 5B shows a top view of spatial filter 526. The assembly 500 includes at least one spatial filter 526 having a length, L, disposed along the longitudinal axis, x, of a flow path detection region 523b and a width, W, along a lateral axis, y, of the flow path detection region 523b. The spatial filter 526 includes mask features 526a, 526b disposed in a pattern that extends at least partially along the length the spatial filter 526 and extending at least partially across the width of the spatial filter 526. In this embodiment, mask features 526a may be referred to as less transmissive (i.e., opaque) and mask features 526b may be referred to as more transmissive (i.e., clear).

For example, the pattern along the length of the spatial filter may be a repeating pattern, a periodic pattern, a random pattern or any other pattern. The assembly 500 in FIG. 5A includes at least one detector 530 positioned to detect light emanating from the objects 501, 502, 503. The detected light has a component along a detection axis, z-axis, that makes a non-zero angle with respect to the longitudinal and lateral axes. The detected light is time modulated according to the mask features as the objects move along the flow path 523 in the flow direction 523a. The detector 530 is configured to generate a time-varying electrical signal in response to the detected light that includes information about characteristics of the objects, such as the depth position and/or depth trajectory of the objects in the flow path 523. The assembly 500 may include an analyzer 540 configured to determine a depth of the object in the detection region along the detection axis based on the time varying signal generated by the detector 530.

For example, as objects 501, 502, 503 move along a flow path within detector region 523b, the particles emanate light in all directions. The light emanating from the objects 501, 502, 503 interacts with a spatial filter 526. The light emerges from the spatial filter 526 through the clear features 526b1, 526b2, 526b3 in cones of light 501e, 502e, 503e and the light is blocked by the spatial filter 526 by opaque features 526a1, 526a2, 526a3, and 526a4. As shown in FIG. 5A, object 501 is traveling in flow channel at a trajectory depth d1, object 502 is traveling at trajectory depth d2, and object 503 is traveling at trajectory depth d3. Light emanating from object 501 emerges from the spatial filter 526, having passed through clear mask feature 526b1 in cone 501e, which has a cone angle of θe1. Light emanating from object 502 emerges from the spatial filter 526 at clear mask feature 526b2 in cone 502e, which has a cone angle of θe2. Light emanating from object 503 emerges from the spatial filter 526 at mask feature 526b3 in cone 503e, which has a cone angle of θe3.

Light emanating from object 501 at an angle greater than or equal to θe1 but less than or equal to blocking angle θb1 is blocked by the spatial filter 526 by opaque features 526a1 and 526a2. Some light emanating from object 501 at an angle greater than θb1 can emerge from clear features 526b2, 526b3 and light emanating from object 501 is also blocked by opaque features 526a3, 526a4.

Light emanating from object 502 within cone 502e having cone angle θe2 passes through clear feature 526b2. Light emanating from object 502 at an angle greater than or equal to θe2 but less than or equal to θb2 is blocked by the spatial filter 526 opaque features 526a2 and 526a3. Some light emanating from object 502 at an angle greater than θb2 can emerge from clear features 526b1, 526b3, however, light emanating from object 502 is also blocked by opaque features 526a1, 526a4.

Light emanating from object 503 within cone 503e having cone angle θe3 passes through clear feature 526b3. Light emanating from object 503 at an angle greater than or equal to θe3 but less than or equal to θb3 is blocked by the spatial filter 526 by opaque features 526a3 and 526a4. Some light emanating from object 503 at an angle greater than θb3 can emerge from clear features 526b1, 526b2, however, light emanating from object 503 is also blocked by opaque features 526a1, 526a2. The cone angles θe1, θe2, θe3 of the cones 501e, 502e, 503e are inversely related to the depth of the objects, and θe1>θe2>θe3 for d1<d2<d3. The cone angles θb1, θb2, θb3 of the blocking cones 501b, 502b, 503b are inversely related to the depth of the objects, and θb1>θb2>θb3 for d1<d2<d3.

Figure 5C:
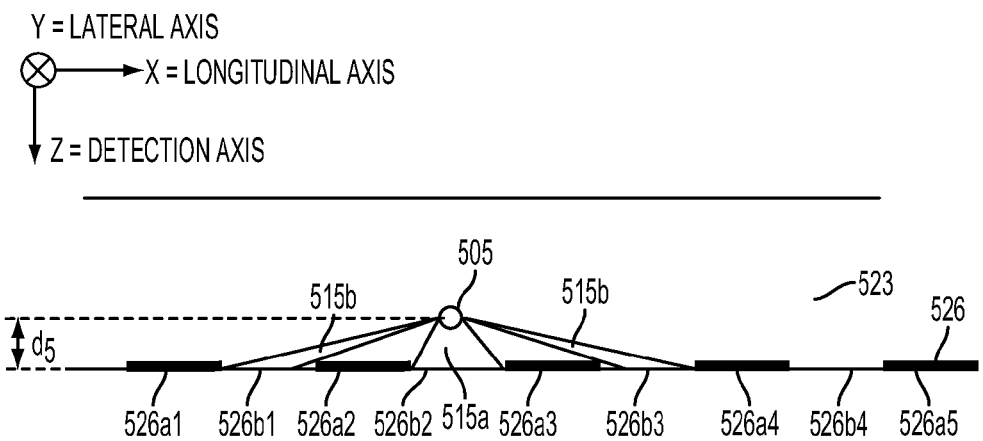
Figure 5D:
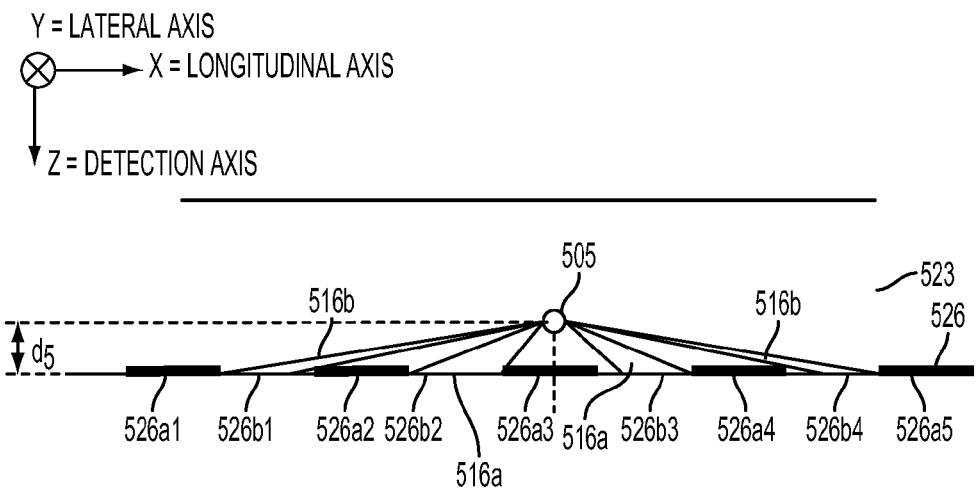

FIGS. 5C and 5D illustrate an object 505 moving through along flow path 523 at a trajectory depth d5 along the detection axis, z. FIG. 5C illustrates the object 505 at the moment when it is passing over clear feature 526b2 of the spatial filter 526. Object 505 emanates light 515a that passes predominantly through clear feature 526b2 and also some light 515b emanating from object 505 passes through clear features 526b1 and 526b3. Due to the proximity of object 505 to the spatial filter 526, very little or no light passes through clear feature 526b4. FIG. 5D illustrates the object 505 at the moment when it is passing over opaque feature 526a3 of the spatial filter 526. Object 505 emanates light 516a that passes through clear features 526b2, 526b3. Due to the proximity of object 505 to the spatial filter 526, very little light 516b from object 505 passes through clear features 526b1, 526b4.

Figure 5E:
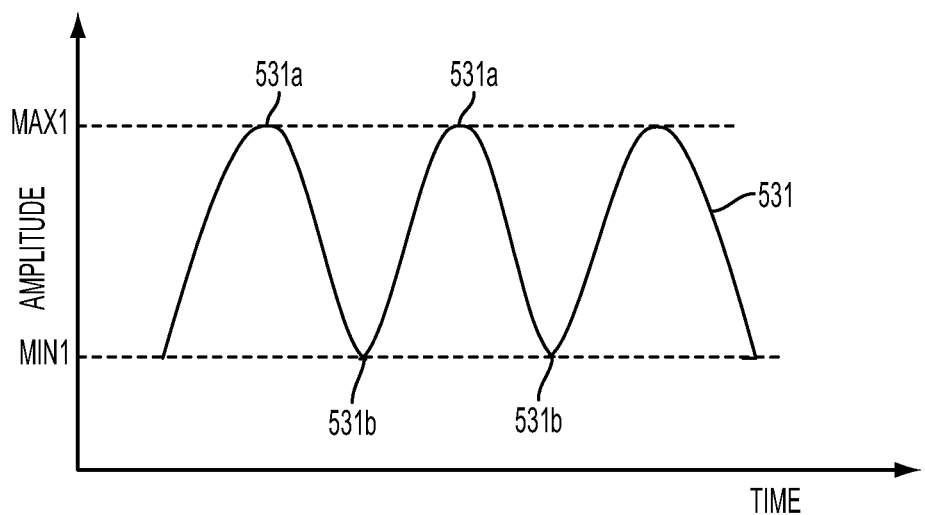

FIG. 5E is a graph of a portion of an idealized time modulated detector signal 531 generated by the movement of object 505 relative to the spatial filter 526. The amplitude of the signal 531 increases and decreases as the object 505 passes over clear and opaque features, respectively. The peak regions include maximum peaks 531a of the signal 531 that have a maximum value of Max1 due to the amount of light emanating from the object 505 that passes through the clear features as the object 505 passes over the clear features as shown in FIG. 5C. The trough regions include minimum peaks 531b of the signal 531 have an offset of Min1 because of the emanating light that passes through clear features as the object 505 passes over the opaque features as illustrated by FIG. 5D.

Figure 5F:
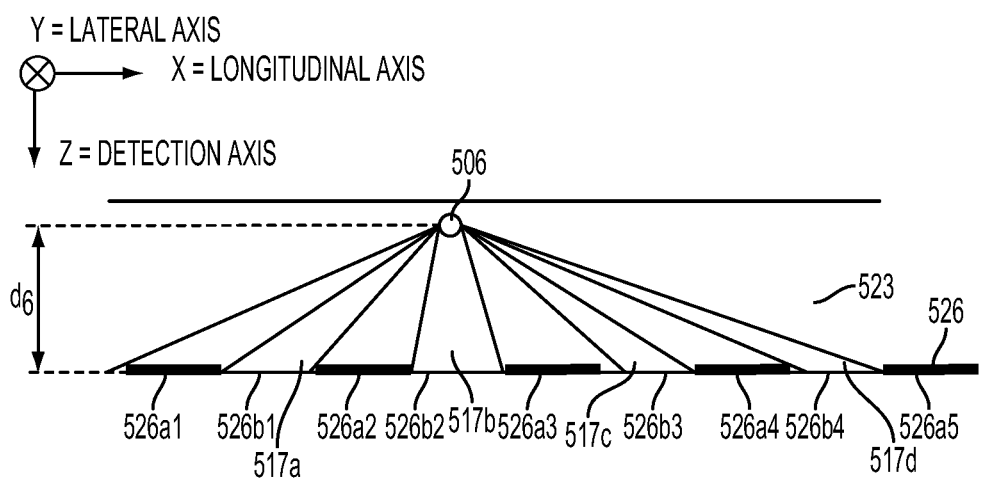
Figure 5G:
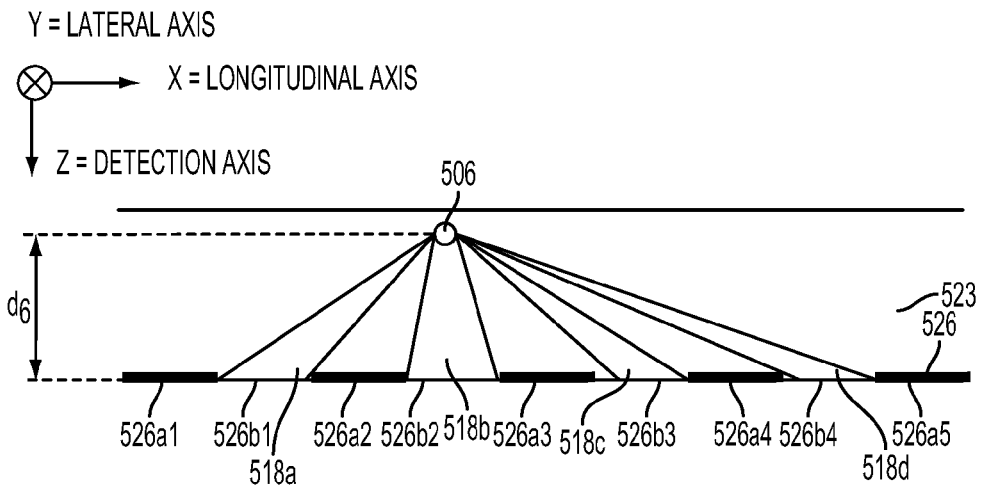

FIGS. 5F and 5G illustrate an object 506 moving through along flow path 523 at a trajectory depth d6 with respect to the detection axis, z. FIG. 5F illustrates the object 506 when it is passing over clear feature 526b2 of the spatial filter 526. Light 517b emanating from the object 506 passes through clear feature 526b2. Some light 517a, 517c from object 506 passes through clear feature 526b1 and 526b3. Due to the distance between object 506 and the spatial filter 526, some light 517d passes through clear feature 526b4.

FIG. 5G illustrates the object 506 when it is passing over opaque feature 526a3 of the spatial filter 526. Object 506 emanates light 518b, 518c that passes through clear features 526b2, 526b3 and also some light 518a, 518d from object 506 passes through clear features 526b1 and 526b4.

Figure 5H:
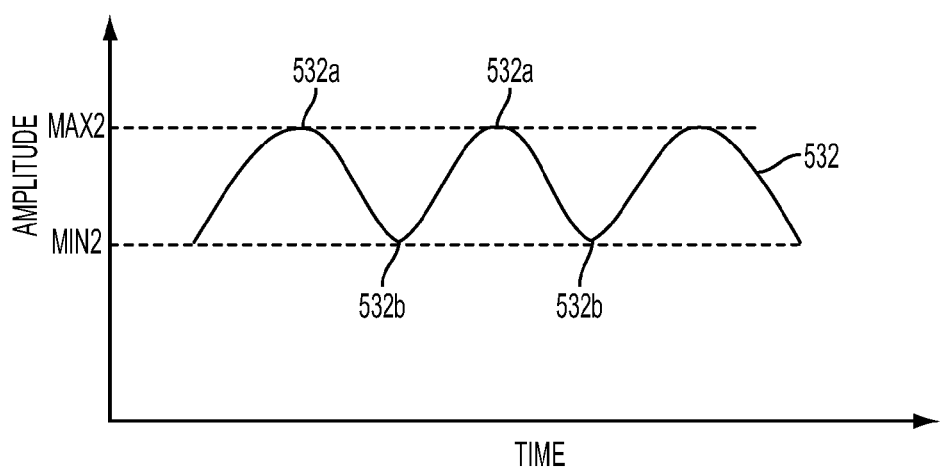

FIG. 5H is a graph of a portion of an idealized time modulated detector signal 532 generated by the movement of object 506 relative to the spatial filter 526. The amplitude of the signal 532 increases and decreases as the object passes over clear and opaque features, respectively. The peaks 532a of the signal 532 have a maximum value of Max2 due to the amount of light emanating from the object 506 that passes through the clear features as the object 506 passes over a clear feature as shown in FIG. 5G. The valleys 532b of the signal 532 have an offset of Min2 because of the emanating light that passes through clear features as the object 506 passes over an opaque feature as shown in FIG. 5H. For d6>d5, Max2<Max1 and Min2>Min1. The differences in the peak maxima and minima occur due to the blocking and emitting cones that result from the interaction of the emanating light with the mask. The peak maxima and peak minima of the time varying signal can be analyzed to determine the trajectory depth in the flow channel of the object along the detection axis of the flow path as indicated by FIGS. 5E and 5H and as discussed in more detail below. The discussion in connection with FIGS. 5A through 5H presumes a uniform light source illuminating the objects. In addition, the discussion presumes that light exiting from the detection area 523b through the clear features 526b does not experience any change in index of refraction. In many embodiments, the illumination light is non-uniform over the detection area 523b which superimposes a similar non-uniformity on the time varying output signal from the detector. Differences in refractive index between the materials disposed on either side of the clear features 526b of the mask change the angle of the light exiting the mask according to Snell's law, $\sin\theta_1/\sin\theta_2 = n_2/n_1$, where $n_1$ is the index of refraction of the material within the flow path detection region 523b, $\theta_1$ is the angle of light before the light exits through the clear features of the mask 526, $n_2$ is the index of refraction of the material between the flow path material and the detector, and $\theta_2$ is the angle of the light after it exits through the mask.

Figure 5I:
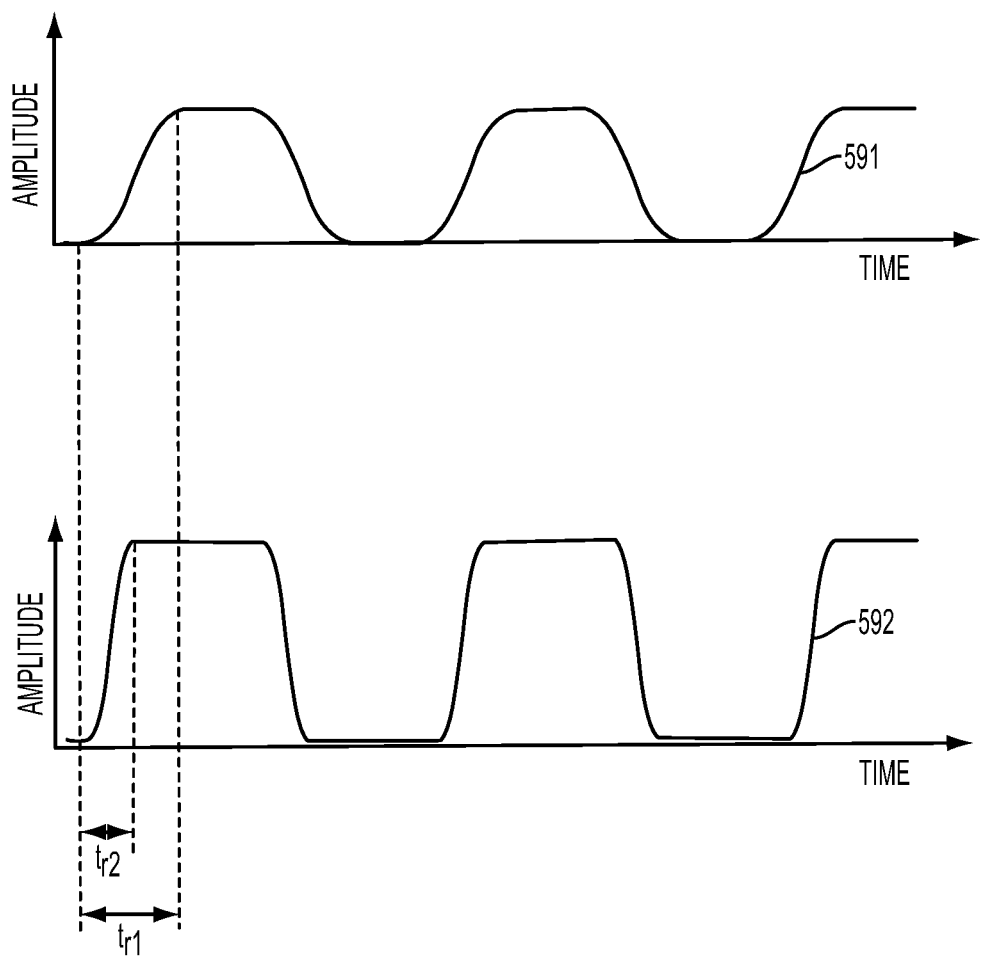

Furthermore, consider the pulses generated by light emanating from an object that is traveling very close to the mask features such that the trajectory depth is small when referenced from the position of the mask. The resulting signal, illustrated as signal 592 of FIG. 5I, will become closer to a square wave, instead of the sinusoidal shape shown in FIG. 5E. Because of the geometry resulting from the close proximity of the object to the mask features when the object is close to the spatial filter, emanating light predominantly reaches the detector through one clear opening directly below the object. The angles are such that light going through other mask openings are at such shallow angles, much of the light will be directed away by the opaque features and fail to reach the detector. When the object is close to the mask, the emanating light either reaches the detector when the particle is over a clear feature, or is blocked when the particle is over an opaque feature, resulting in a predominantly square wave shape as illustrated by signal 592. The actual wave shape may be affected by the object length relative to the mask feature length as described and illustrated in concurrently filed U.S. patent application Ser. No. 14/181,530, which is incorporated by reference in its entirety.

When the object is farther from the mask, emanating light from the object reaches the detector through a clear opening directly below the object and a portion of the light reaches the detector through other clear features. Because the object is farther from the mask features, the emanating light generates in a detector signal 591 that includes pulses having a longer rise time, $t_{r1}$, when compared to the rise time, $t_{r2}$, of pulses of the signal 592 generated when the object is closer to the mask features. As the object moves farther away from the mask features, the pulses more and more resemble a sine wave and are less and less square wave shaped. Thus, the shape of the signal generated by the emanating light, e.g. rise times and/or fall times of the pulses, can be analyzed in addition or alternatively to the peak minima and maxima to determine the trajectory depth in the channel.

Figure 6A:
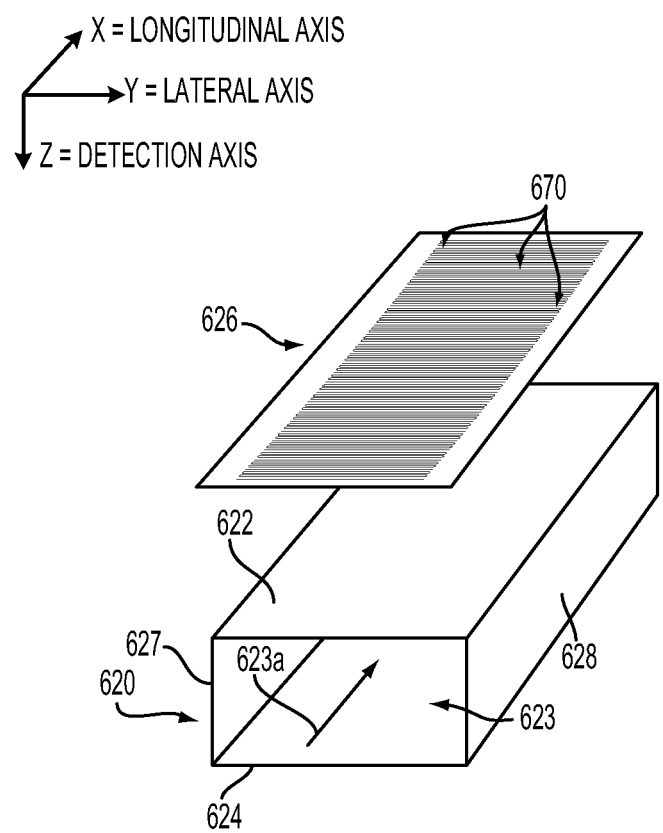
FIG. 6A is a perspective view of a spatial filter having mask features patterned according to an example embodiment.

In some embodiments, the spatial filter selected for use may enhance signal processing for depth analysis. FIG. 6A illustrates a spatial filter 626 with a pattern of features that produces an output signal having two frequency components. Features of the two frequency components can be analyzed in the time domain, or can be converted to the frequency domain, e.g., using a Fourier transform, for analysis.

FIG. 6A shows a perspective view of a portion of a fluidic device 620 and spatial filter 626. The fluidic device 620 includes a flow channel 623 having a flow direction 623a and confining members 622, 624, 627, and 628. Although the confining members 622, 624, 627, and 628 are positioned to define a flow path 623, in other embodiments one or all of the confining members 622, 624, 627, and 628 may not be used. The flow direction 623a aligns generally with the x-direction of the Cartesian coordinate system illustrated in FIG. 6A. In the embodiment shown, the spatial filter 626 is arranged at a distance from the confining member 622. In other embodiments, the spatial filter 626 may be arranged within the flow channel 623, mounted to any confining members or positioned relative to any of the confining members. A detector (not shown) may be positioned in any appropriate location to sense time modulated light passing through the filter 626 that has a component along the detection axis, z.

In FIG. 6A, the spatial filter 626 is arranged in the x-y plane of the Cartesian coordinate system. The spatial filter 626 has a plurality of mask features 670 arranged in a pattern. In particular, the mask features 670 have repeating periodic patterns in the x-direction (referred to herein as the longitudinal direction) and at least partially extend along the lateral direction of the mask 626. Additionally, as shown in FIG. 6C, each of the mask features 670 has a length of either $L_1$ or $L_2$ in the x-direction. The lengths $L_1$ and $L_2$ remain constant as the mask features 670 extend laterally across a width of the spatial filter 626. In some embodiments, the ratio of the lengths $L_1$ to $L_2$ is between 9:2 and 10:1. However, the ratio of the lengths $L_1$ to $L_2$ may vary depending upon design and other criteria including, for example, object size, object velocity, and ease of signal processing.

Figure 6B:
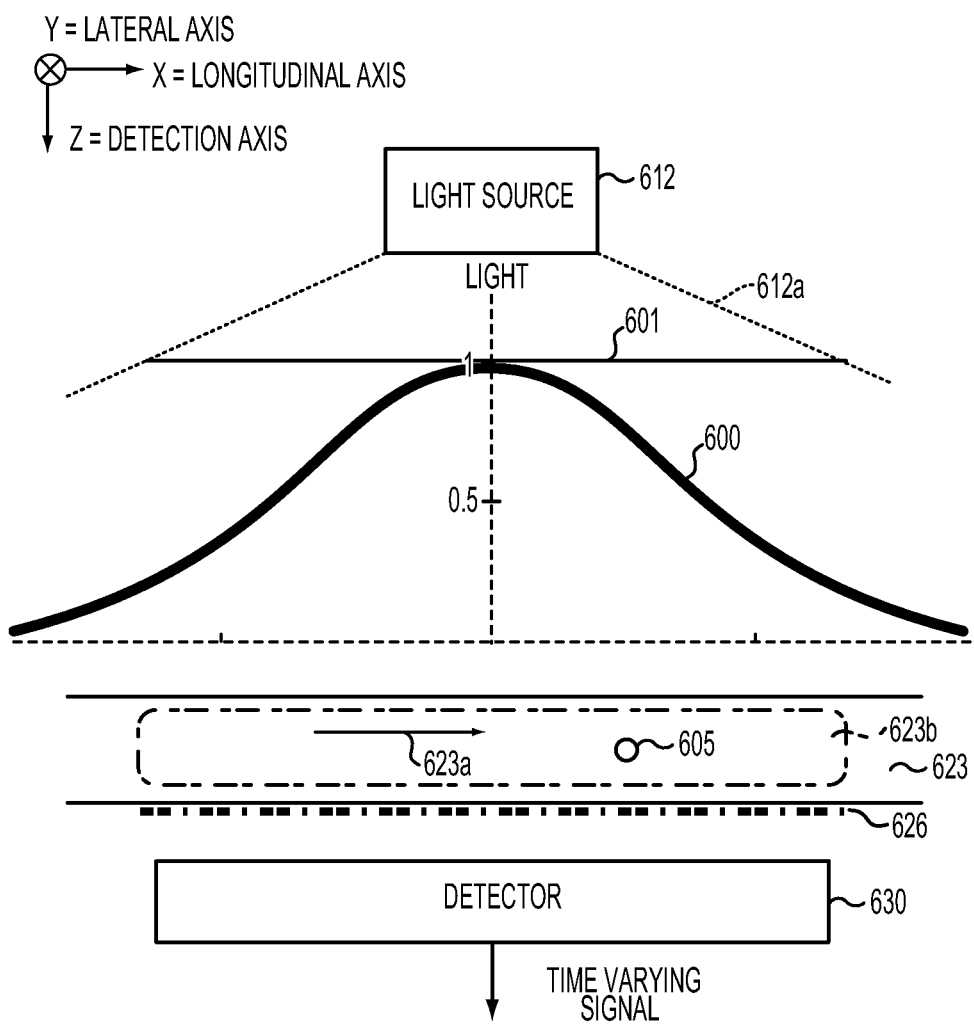
FIG. 6B shows the spatial filter of FIG. 6A arranged in relation to a light source, a detection region of a flow path, and a detector.
Figure 6C:
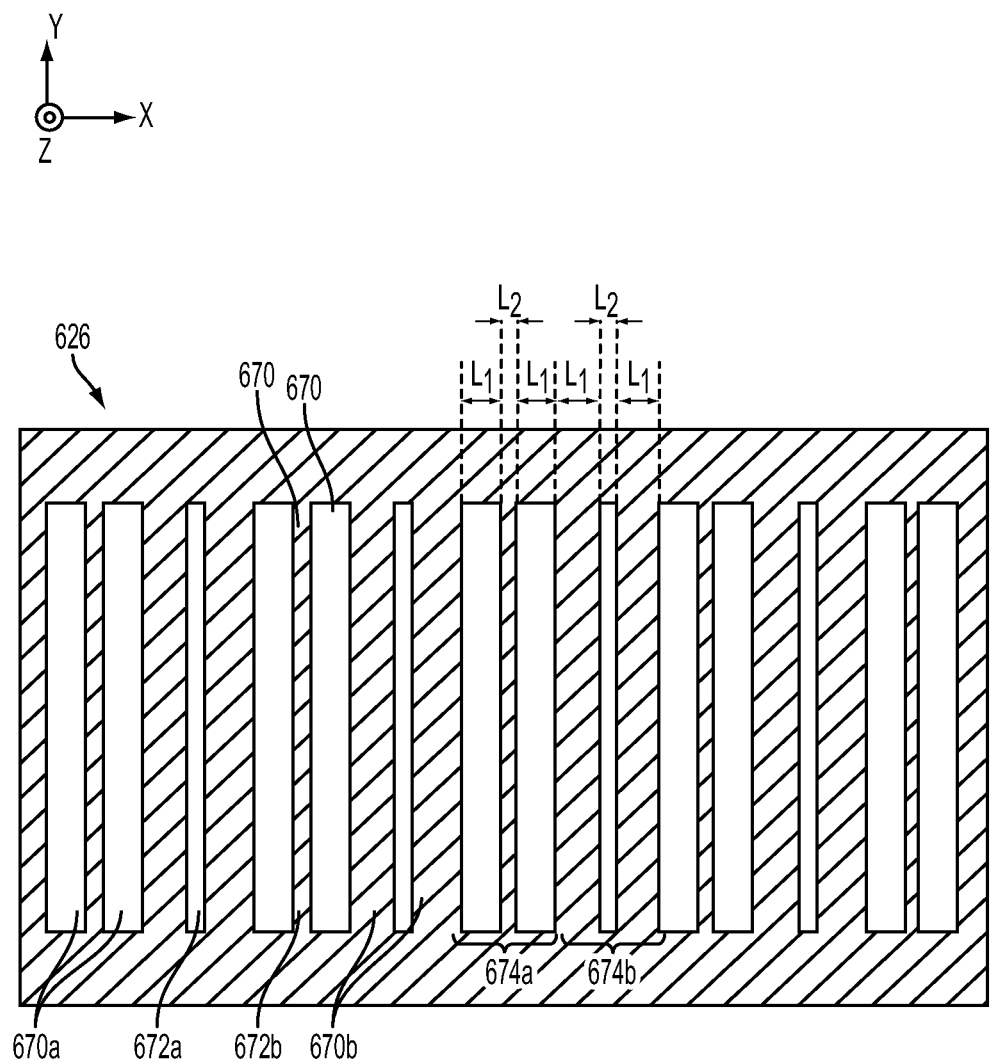
FIG. 6C is an enlargement of the spatial filter of FIG. 6A.

FIG. 6B shows the spatial filter 626 arranged in relation to a light source 612, detection region 623b of a flow path 623, and a detector 630. Objects move in the detection region 623b along a flow direction 623a and emanate light. A light source 612 provides illuminating light 612a that illuminates the objects in the detection region 623b. FIG. 6B shows two possible intensity profiles 600, 601 of illuminating light 612a. The intensity profile 601 has substantially uniform intensity across the detection region 623b. For example, intensity profile 601 could be provided by the sun or another wide area source. The intensity profile 600 has an approximately Gaussian distribution. For example, intensity profile 600 could be provided by small area source or point source. Profiles 600 and 601 are but two possible profiles and in various embodiments the profile of the illuminating light may vary from the uniform and Gaussian profiles illustrated. When the illuminating light is non-uniform, the shape of the profile of the illuminating light 612a is imposed on emanating light emanating from the objects and on the time varying output signal 631.

FIG. 6C is a plan view of an enlarged portion of the spatial filter 626 of FIG. 6A illustrating the mask features 670 in greater detail. Mask features 670 include first mask features 670a, 672a that have first transmission characteristics, and second mask features 670b, 672b that have second transmission characteristics different from the first transmission characteristics. For example, features 670a, 672a may be more transmissive for a particular wavelength pass band than features 670b, 672b. In the illustrated example, the more transmissive features 670a have lengths $L_1$ in the x-direction while the more transmissive features 672a have lengths $L_2$ in the x-direction. In the embodiment shown, the less-transmissive features 670b have lengths $L_1$ in the x-direction while the less-transmissive features 672b have lengths $L_2$ in the x-direction.

In FIG. 6C, the mask features 670 alternate between first and second sets of features 674a, 674b in the x-direction. The first and second sets of features 674a, 674b provide for two different frequency components in the time modulated light (and the time varying electrical signal of the detector) as will be discussed subsequently. The first set of features 674a is comprised of two of the transmissive regions 670a arranged to either side of a single one of the less-transmissive regions 672b. The second set of features 674b is comprised of two of the less-transmissive regions 670b arranged to either side of a single one of the transmissive regions 672a.

Figure 6D:
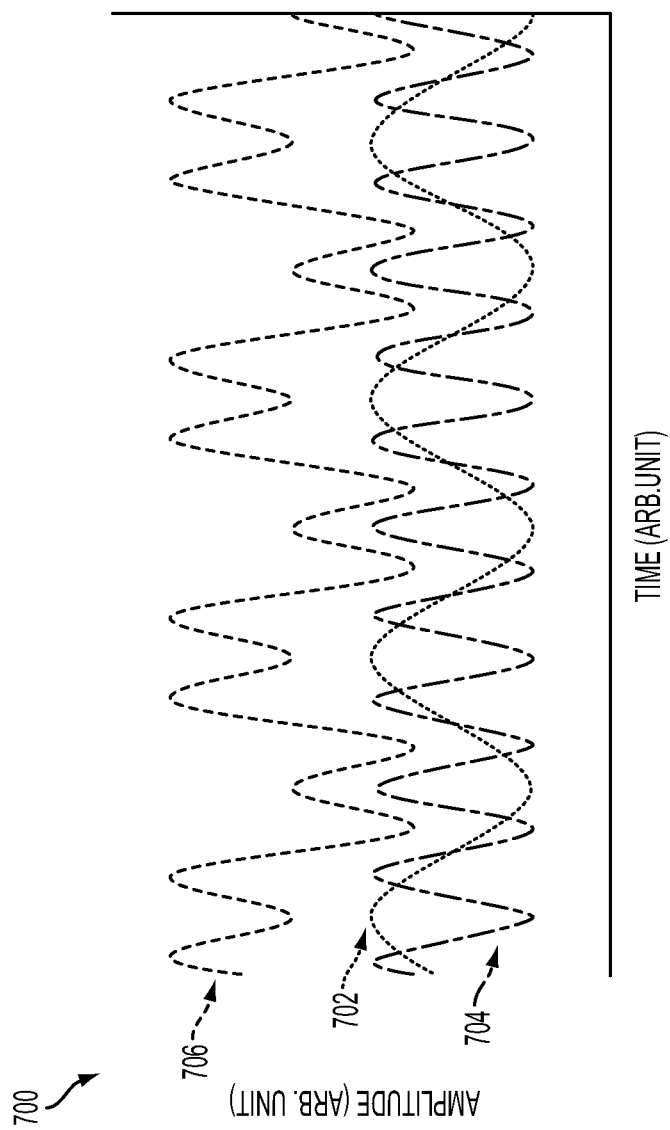
FIG. 6D is a plot of output signals that result from light modulated by the spatial filter of FIG. 6A.

FIG. 6D is a simplified plot 700 of the electrical signals generated in response to the modulated light that has passed through the mask features 670 of the spatial filter 626 of FIGS. 6A and 6C. The simplified plot 700 presumes that the illuminating light has a uniform profile and illustrates that the configuration of the mask features 670 produces first and second signal components 702 and 704 that are superimposed in the resulting time domain electrical signal 706.

In FIG. 6D, first and second signal components 702 and 704 may both have a sinusoidal pattern. Signal components 702 and 704 represent a mathematical decomposition of electrical signal 706 which is generated in response to the modulated light that has passed through the mask features 670 of the spatial filter 626 of FIGS. 6A and 6C. The first sinusoidal signal component 702 is associated with the transmissive regions 670a (see, FIG. 6C) and the corresponding less-transmissive regions 670b (FIG. 6C) while the second signal component 704 is associated with the transmissive regions 672a (FIG. 6C) and the corresponding less-transmissive regions 672b (FIG. 6C).

The electrical signal 706 is the sum of the first signal component 702 having a first frequency and the second signal component 704 having a second frequency and is the result of alternating the first set of features 674a (FIG. 6C) with the second set of features 674b (FIG. 6C). In the embodiment shown in FIG. 6D, the first frequency differs from the second frequency. In various embodiments, the second frequency may be a multiple of the first frequency, e.g., three times the first frequency as shown in this example. In some embodiments, the analyzer may be configured to determine the trajectory depth in the flow path 623 of the object 605 by analyzing the morphology of the signal 706 in the time domain. In some embodiments, the analyzer may be configured to determine the trajectory depth in the flow path 623 of the object 605 by transforming the signal 706 from the time domain to the frequency domain and analyzing the transformed signal in the frequency domain.

Figure 6E:
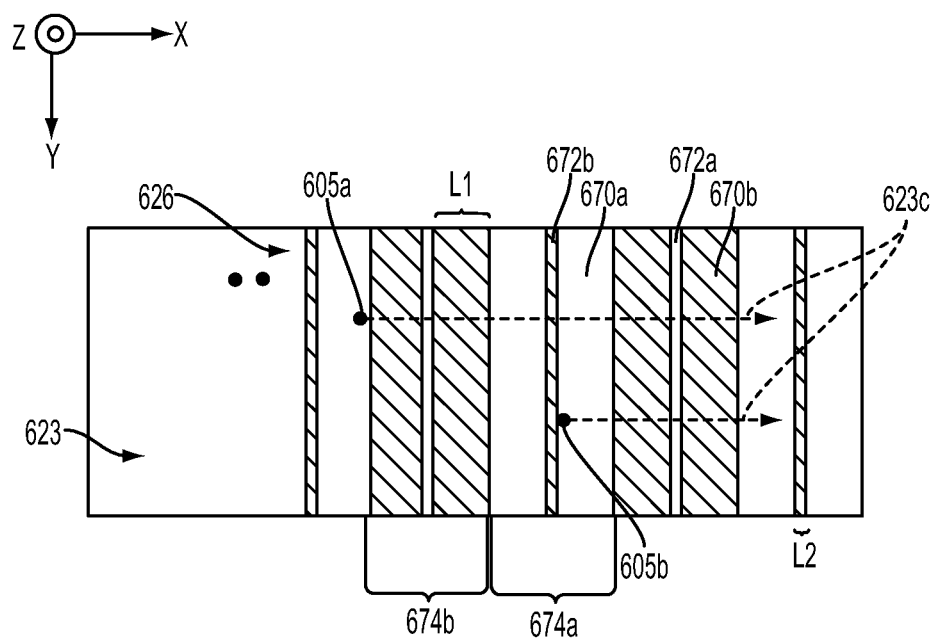
FIGS. 6E and 6F, respectively, are top and side views of the spatial filter of FIG. 6A disposed over a flow path containing two light emanating objects.
Figure 6F:
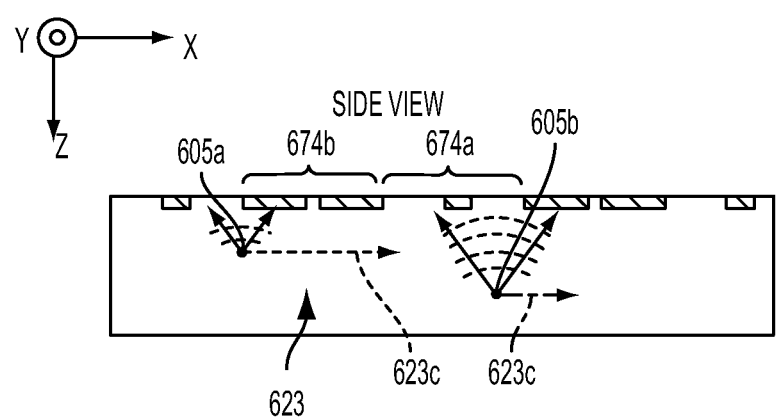

FIGS. 6E and 6F show, respectively, a top view and a side view of the filter 626 design of FIGS. 6A and 6C. Spatial filter 626 is used with illuminating light having an approximately Gaussian profile in an exemplary application to determine the trajectory depths in the flow path 623 (possibly along with other characteristics) of objects 605a and 605b. In FIGS. 6E and 6F, the objects 605a and 605b are disposed within a flow channel 623 and are moving in a flow direction 623a under the filter 626. In this embodiment, the detector (not shown) would be positioned above the filter 626 to sense light emanating from the objects that has interacted with the filter 626. Thus, the objects 605a and 605b travel below the features 670 comprised of the first set of features 674a and the second set of features 674b.

Figure 6G:
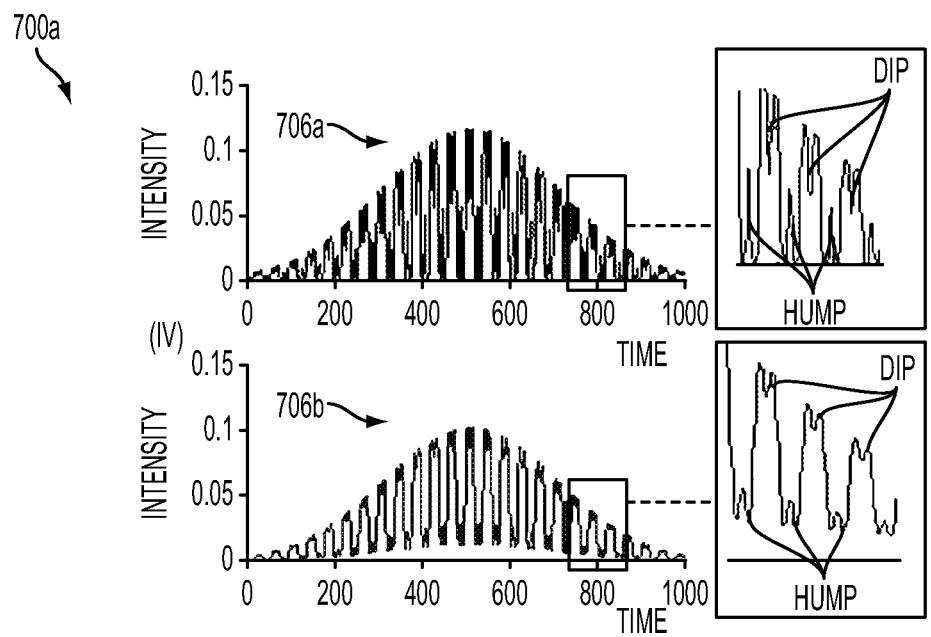
FIG. 6G illustrates plots of the time-varying electrical signals generated in response to the modulated light from each of the two objects moving close to/away from the spatial filter of FIG. 5D.

FIG. 6G shows plots 700a of the time-varying electrical signals 706a and 706b generated in response to the modulated light sensed from each of the objects 605a and 605b moving relative to the spatial filter 626 at different depths in the flow channel 623. Object 605a is moving along the flow channel 623 at a shallower depth (referenced from the position of the spatial filter) in the flow channel 623 than object 605b, closer to the spatial filter 626 than object 605b. Object 605b is moving along the flow channel 623 at a greater depth in the flow channel 623 than object 605a, farther from the spatial filter 626 than object 605a.

Signal 706a corresponds to sensed light from object 605a which is disposed at a shallower depth within the flow channel 623 than object 605b relative to filter 626 and detector (not shown). Signal 706b corresponds to sensed light object 605b which is disposed at a greater depth within the flow channel 623 than object 605a relative to filter 626 and detector (not shown).

As shown in the enlargement of the signal 706a in FIG. 6G, the signal 706a includes "dips" in the peak region and "humps" in the trough region. Similarly, the signal 706b includes "dips" in the peak region and "humps" in the trough region. In this particular embodiment, peak and valley regions correspond to the first frequency component and the dips and humps correspond to the second frequency component. The dips are caused by the less-transmissive regions 672b within the first set of mask features 674a and the humps are caused by the more transmissive regions 672a within the second set of mask features 674b.

The signal 706a has an intensity profile with shorter transition times between peak regions and trough regions and is more sensitive to the more transmissive regions 672a and the less-transmissive regions 672b since more emanating light from object 605a is transmitted or blocked by the regions 672a and 672b when compared with emanating light from object 605b. This phenomenon results in a larger dip in the middle of the peak regions and larger humps in the middle of trough regions of the signal 706a relative to the dips and humps of signal 706b.

For each signal 706a and 706b, the analyzer may be configured to determine the trajectory depths in the flow channel 623 of the objects 605a, 605b along the detection axis, z, by analyzing the signals 706a, 706b in the time domain. In such an analysis, the analyzer circuitry may be configured to determine the amplitudes of the dips and/or humps and/or to determine the amplitude of the peak regions and the trough regions. In some embodiments, the analyzer is configured to compare the amplitudes of the dips and/or humps to the amplitude of the peak region and/or trough region to determine the trajectory depth in the flow channel 623 of the object 605a and 605b. This determination is informed by mask features 670, which have a known size and pattern. Thus, the output signals 706a and/or 706b may be dependent on the known mask pattern to allow for extraction of desired information including depth. The determination of the trajectory depth in the flow channel may additionally be informed by, for example, comparing characteristics of the output signals 706a and/or 706b to reference output signals with known object light intensity, velocity, object size, and/or the known trajectory depth in the flow channel of other reference objects.

For each signal 706a and 706b, the analyzer may be configured to determine the trajectory depths in the flow channel of the objects 605a, 605b along the detection axis, z, by converting the time varying signals 706a, 706b to the frequency domain, for example, by using a Fourier transform or fast Fourier transform (FFT). The analyzer then determines the trajectory depths in the flow channel of the objects through analysis of the transformed signals. FIG. 6H shows plots 800 of the amplitudes of the electrical signals 706a and 706b converted to the frequency domain. Plot 802 corresponds to signal 706a for object 605a while plot 804 corresponds to the signal 706b for object 605b. Intensity peak $I_2$ corresponds to the amplitude of the peak and trough regions of the output signal and result from the more transmissive regions 670a (FIG. 6C) and the less-transmissive regions 670b (FIG. 6C) of the filter 626. Intensity peak $I_3$ corresponds to the amplitude of the humps and dips that result from the more transmissive regions 672a (FIGS. 6C and 6E) and the less-transmissive regions 672b (FIGS. 6C and 6E) of the filter 626. As shown in plots 800, the intensity peak $I_2$ of plot 802 is slightly larger than the intensity peak $I_2$ of plot 804 due to the slightly larger peaks/valleys in signal 706a. As shown in plots 800, the intensity peak $I_3$ of plot 802 is much larger than the intensity peak $I_3$ of plot 804 due to the much larger dips/humps in signal 706a. The analyzer can be calibrated to determine trajectory depth in the flow channel based on the amplitude of the intensity peaks $I_2$ and/or $I_3$ and/or can be calibrated to determine trajectory depth in the flow channel based on a ratio of $I_2$ and $I_3$. Utilizing the frequency domain analysis including intensity peaks $I_2$ and/or $I_3$ can aid in the determination of the trajectory depth in the flow channel of the object. For example, analysis using the intensity peaks $I_2$ and $I_3$ allows for direct comparison in the frequency domain of the amplitude of the peak and/or trough regions with the amplitude of the humps and/or dips.

Figure 7:
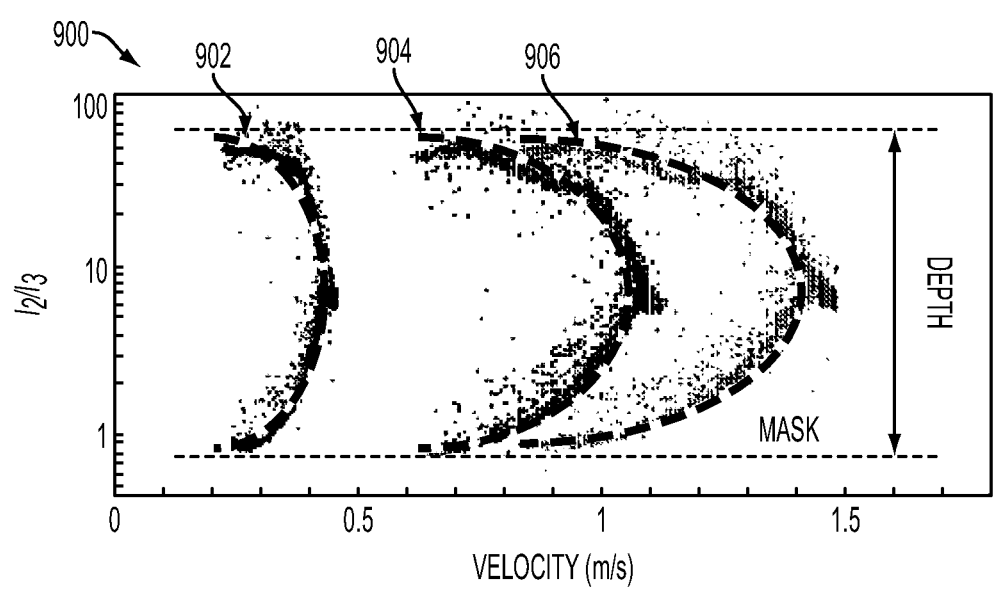
FIG. 7 illustrates $I_2/I_3$ Fourier amplitude peaks measured on a logarithmic scale plotted against velocity and depth for various experiments.

Analysis of the trajectory depth in the flow channel of the object can be performed using a ratio of the intensity peak $I_2$ relative to the intensity peak $I_3$ as illustrated in the plot 900 of FIG. 7. Plot 900 illustrates $I_2/I_3$ intensity peaks measured on a logarithmic scale plotted against velocity and trajectory depth in the flow channel. Data sets 902, 904, and 905 were generated from three separate sets of experiments with more than 2500 object events each are captured. These data sets 902, 904, and 905 verify the robustness of the $I_2/I_3$ matrix methodology. Parameters including fluidic flow rate and data acquisition rate were altered in order to disturb the fluorescence intensity obtained, which is usually obtained and utilized as a matrix in flow cytometry. The analyte flow pump rate of 1.8 ill/min (micro-liters per minute) is sandwiched between two 30 μl/min sheath flows and data acquisition rate is set to 400 kHz for the first data set 902. The second data set 904 was performed with parameters of 4.5 μl/min analyte, 75 μl/min sheath and data acquisition rate 600 kHz. The third data set 906 was performed with parameters of 6 ill/min analyte, 100 μl/min sheath and data acquisition rate 600 kHz. The higher fluidic speed and higher acquisition rate lead to a smaller intensity value. Although both $I_2$ and $I_3$ vary with data sets 902, 904, and 906, using the $I_2/I_3$ ratio produces an almost identical ratio value range from the three data sets 902, 904, and 906. By utilizing mask features that produce the dip and hump phenomenon, many disturbance and variations effect the signals will likely be canceled out in the matrix of $I_2/I_3$. The data sets 902, 904, and 906 show that observation of the $I_2/I_3$ ratio in log scale is very relevant to the known laminar flow velocity profile along the channel depth. This is mainly attributed to the fact the amplitude of intensity profile on mask features decreases exponentially with distance away from the mask features within the flow channel. Thus, the $I_2/I_3$ ratio can be a powerful metric to measure the depth of the object within the flow channel.

Figure 8A:
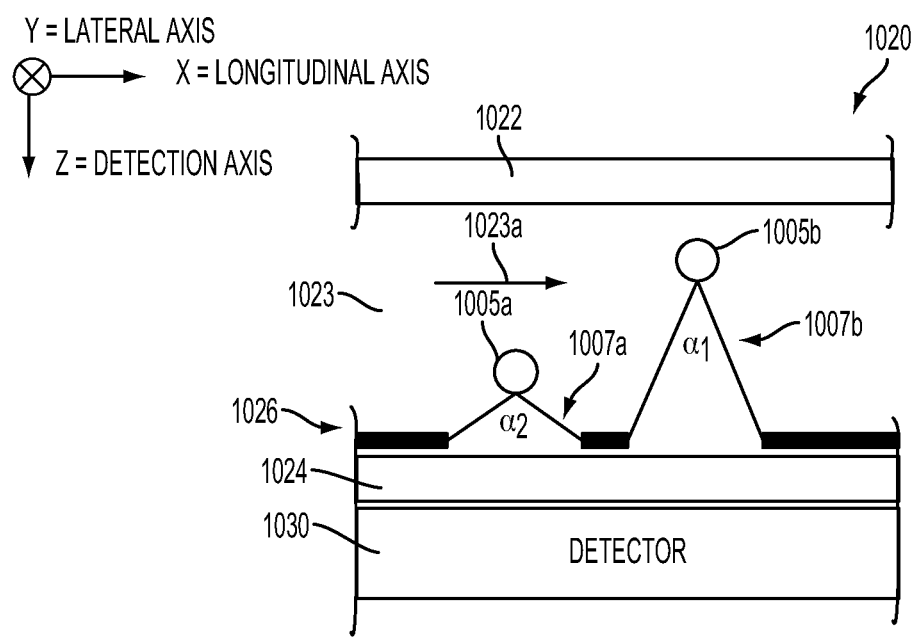
FIG. 8A is a schematic view of a portion of a fluidic device, spatial filter, and detector with objects having cones of light emanating from them.

FIG. 8A is an illustration of a portion of a fluidic device 1020, spatial filter 1026, and detector 1030. The fluidic device 1020 includes a flow channel 1023 with objects 1005a, 1005b disposed therein at differing depths. The objects 1005a, 1005b have light 1007a, 1007b, respectively, emanating therefrom as they move along the flow channel 1023 in a flow direction 1023a. As shown in FIG. 8A, the emanating light 1007a, 1007b from each of the objects 1005a, 1005b interacts with the filter 1026 to provide cones of light $\alpha_1$ and $\alpha_2$ that emerge from transmissive regions of the filter 1026 and fall on the detector 1030. The size and angles of the cones of light $\alpha_1$ and $\alpha_2$ are related to the trajectory depth of the objects 1005a, 1005b within the flow channel 1023 among other factors. Thus, the electrical signal produced by the detector 1030 includes at least one characteristic indicative of the angle of the cones of light $\alpha_1$ and $\alpha_2$. An analyzer (not shown) may be configured to determine the depth of the objects 1005a, 1005b based on the signal characteristic indicative of the angle of the cones of light $\alpha_1$ and $\alpha_2$.

For example, for an excited object emitting an ideal spherical wave of fluorescence, the emanating light 1007a, 1007b would project a Gaussian distribution of optical intensity profile on the plane of filter 1026 governed by the equation $$u(x, y) = \sqrt{\frac{2}{\pi}} \frac{1}{w} e^{-\frac{(x^2+y^2)}{w^2}},$$

where u is the Gaussian transverse amplitude with unity power flow, w is the spot size. However, in most cases only a portion of the emanating light 1007 comprising, for example, cones of light $\alpha_1$ and $\alpha_2$ would pass through portions of the filter 1026 and other intervening components (e.g., bounding member 1024) and fall on the detector 1030. Any intervening components between the objects 1005a, 1005b and detector 1030 would cause refraction of the cones of light $\alpha_1$ and $\alpha_2$ at the interface of the components. This refraction is governed by known principles according to Snell's law. Thus, using Gaussian distribution of optical intensity profile, the known characteristics of the filter 1026, the measured characteristics of the electrical signal, and Snell's law one can determine the angle of the cones of light $\alpha_1$ and $\alpha_2$.

Figure 8B:
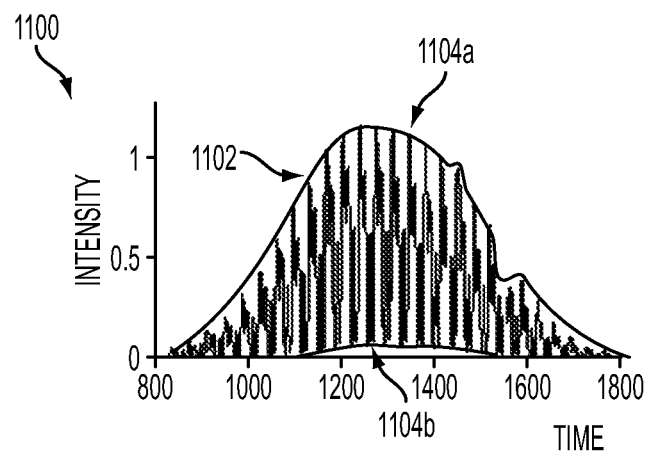
FIG. 8B is a plot of a modulation envelope that results from the passage of one of the objects of FIG. 8A with cones of light $\alpha_2$ through the flow channel past detector.
Figure 8C:
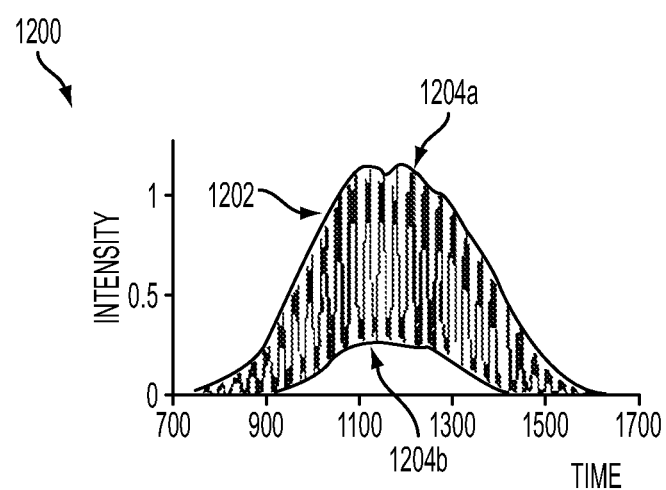
FIG. 8C is a plot of a modulation envelope that results from the passage of one of the objects of FIG. 8A with cones of light $\alpha_1$ through the flow channel past detector.

FIG. 8B shows a plot of the signal 1100 including a time modulation envelope 1102 that results from the passage of the object 1005a (FIG. 8A) with cones of light $\alpha_2$ along the flow path 1023 past detector 1030. The modulation envelope 1102 is disposed between a lower modulation function 1104b comprising the minimum peaks of the troughs of the signal 1100 and an upper modulation function 1104a comprising the maximum peaks of the peaks of the signal 1100. Similarly, FIG. 8C shows a plot of the signal 1200 including a modulation envelope 1202 that results from the passage of the object 1005b (FIG. 8A) with cones of light $\alpha_1$ along the flow path 1023 past detector 1030. The modulation envelope 1202 is disposed between a lower modulation function 1204b comprising the minimum peaks of the troughs of the signal 1200 and an upper modulation function 1204a comprising the maximum peaks of the peaks of the signal 1200.

The modulation envelopes 1102 and 1202 are the signals generated by the detector 1030 of FIG. 8A in response to the sensed light that falls on the detector 1030. The trajectory depth in the flow channel of the objects 1005a, 1005b may be determined based on one or more characteristics of the modulation envelopes 1102 and 1202.

For example, in some embodiments, the trajectory depth in the flow channel of the objects may be determined using the amplitudes of the peaks and/or troughs of the signal and/or the amplitudes of the humps and dips within the peaks and/or troughs as previously discussed.

In some embodiments, the one or more characteristics may be an amplitude, e.g., peak amplitude, of the lower modulation function of the modulation envelope generated by the light emanating from an object. In some embodiments, the one or more characteristics used to determine object depth may be a width, e.g., full width half maximum (FWHM) width, of the lower modulation function of the modulation envelope generated by the light emanating from an object.

As illustrated by FIGS. 8B and 8C, the maximum amplitude of the lower modulation function 1104b, 1204b of the modulation envelope may be non-zero in some cases as the result of emanating light 1007a, 1007b passing through more than one transmissive region of the spatial filter 1026 and reaching the detector even when the object is over a blocking mask feature. The amount of modulation which may be characterized by the maximum value of the lower modulation function 1104b, 1204b can be correlated to the trajectory depth of the objects 1005 within the flow channel 1023.

FIGS. 5 through 8 refer to approaches for determining a trajectory depth position of an object in a flow path with reference the detection axis (also referred to as z-axis and depth axis). The trajectory depth position may be determined based on the time varying signal output from the detector and/or a frequency transform of the detector output signal. It will be appreciated that the time varying signal can be used to determine longitudinal position of the object with reference to the x-axis as well as its trajectory depth position along the z-axis. For example, the analyzer may be configured determine the longitudinal position of the object by analyzing the number of peaks and troughs in the signal, wherein the peak or trough number can be correlated to a longitudinal position. In some embodiments, the analyzer may determine, separately or additionally, the velocity of the object along the x-axis based on the time varying signal and/or based on a frequency transform thereof.

In some embodiments, spatial filter may be configured so that the object position in three dimensions and/or trajectory in three dimensions can be determined. The analyzer can include circuitry that analyzes the detector output signal to determine one or more of the longitudinal position of the object along the x-axis, the lateral position of the object along the y-axis, and the trajectory depth position of the object along the z-axis. In embodiments discussed herein the z-axis corresponds to the axis of detection.

In some embodiments, the spatial filter used for three dimensional position determination may include multiple types of features wherein first features are used to determine position along a first axis and second features, different from the first features, are used to determine position along a second axis. The first features may be disposed in a first portion of the spatial filter and the second features may be disposed in a second portion of the spatial filter. Alternatively, the first and second features may alternate along the spatial filter in the longitudinal direction. For example, the first type of features may be used to determine x-axis position and y-axis position and a second type of features may be used to determine x-axis position and z-axis position.

In other embodiments, the spatial filter may have features, e.g., a single type of features, used to determine the position of the object in three dimensions. In a these embodiments, the same features that are used to determine lateral position can also be used to determined trajectory depth position and longitudinal position, for example.

Measuring position along a reference axis, e.g., the lateral or depth axes, can be accomplished using mask features that have a characteristic that changes along the axis when the changing characteristic of the mask features produces a discernible change in the output signal of the detector. The changing characteristic in the mask features produces a change in phase, frequency, duty cycle, or some other characteristic that is discernible in the detector output signal.

Some examples discussed below include mask features that have at least one edge disposed at an angle with respect to the reference axis along which the object position is determined. The at least one edge is not parallel or perpendicular to the reference axis. For this type of mask feature, the position of the mask feature changes along the reference measurement axis, e.g., the lateral axis. Detector output signals produced by these mask features exhibit phase differences based on the position of the object along the reference measurement axis. Some examples discussed below include mask features that change in frequency with respect to the measurement reference axis. These mask features produce detector output signals having frequencies that depend on the position of the object along the measurement reference axis.

FIG. 9A is an example of a spatial filter 926 that can be used to determine lateral, longitudinal, and trajectory depth positions of an object in a flow path. In this example, the analyzer can make a determination of lateral position of the object based on the phase of the output signal as discussed in more detail below. The analyzer can make a determination of depth position based on techniques previously discussed, such as by analyzing the modulation envelope, e.g., analyzing the lower modulation function, of the detector output signal.

The spatial filter 926 includes features 970 that have two edges 970a that are perpendicular to the lateral axis, y, and two edges 970b that are not parallel or perpendicular to the lateral axis, making an angle with the lateral axis. The interaction of the light emanating from objects 915a, 915b with the edges 970b of the mask features 970 generates output signals 980a, 980b that include a discernible phase difference with respect to lateral positions, $y_a$, $y_b$ of the objects 915a, 915b.

FIG. 9A depicts a first object 915a flowing generally along the longitudinal axis with constant velocity at a lateral position $y_a$, and a second object 915b flowing generally along the longitudinal axis with constant velocity at a lateral position $y_b$. Light emanating from objects 915a, 915b interacts with mask features 971, 970 to produce output signals 980a, 980b. The output signals 980a, 980b shown in FIG. 9A are idealized, and for simplicity ignore the rise and fall times of the signal edges. The velocities of the objects 915a, 915b can be determined from the frequency components in the output signal produced by interaction of light emanating from the objects 915a, 915b with the periodic mask features 970.

The light emanating from objects 915a, 916b interacts with a reference feature 971, parallel to the lateral axis y, generating reference pulses 981a, 981b at time $t_0$. Pulse 982b is produced in the detector output signal 980b at time $t_b$ when light emanating from object 915b interacts with mask feature 970. Pulse 982a is produced in the detector output signal 980a at time $t_0$ when light emanating from object 915a interacts with mask feature 970. Pulse 982a is shifted in time from pulse 982b due to the lateral position of object 915b relative to the lateral position of object 915a. When the velocity of the objects is known, the difference $t_b - t_a$ can be used to determine the relative difference in lateral position of the objects 915a, 915b. The difference $t_b - t_0$ can be used to determine an absolute lateral position of object 915b and the difference $t_a - t_0$ can be used to determine an absolute lateral position of object 915a.

The trajectory depth of objects 915a, 915b may be determined from the interaction of light emanating from particles 915a, 915b with mask features 970 based on the amount of offset of the troughs, as indicated by the amplitude and/or peak of the lower modulation function of the detector output signal, as discussed in connection with FIGS. 5-8. Note that the objects 915a, 915b would not necessarily be flowing along the flow path at the same time as shown in FIG. 9A, but both signals 980a, 980b are shown along the same time axis for comparison of their respective signals.

FIG. 9B illustrates another spatial filter 996 that can be used to determine a three dimensional position of objects along the flow path, i.e., longitudinal position, lateral position, and trajectory depth position. The spatial filter 996 includes mask features 997 useful for determining lateral position of objects in the flow path because the mask features 997 have at least one edge that is not parallel or perpendicular to the lateral axis. These edges produce a phase difference in the output signal due to the timing offset of the pulses produced by interaction between light emanating from objects and the mask features as previously discussed. The mask features 997 are also useful for determining trajectory depth position of objects, e.g., by analyzing the signal characteristics (peaks, troughs, dips and/or humps) in time and/or frequency domains as previously discussed in connection with FIGS. 5-8. For example, the trajectory depth position of objects in the flow channel can be determined based on the amount of offset of the troughs (i.e., the lower modulation function) of the detector output signal, as previously discussed in connection with FIGS. 5-8.

Figure 10:
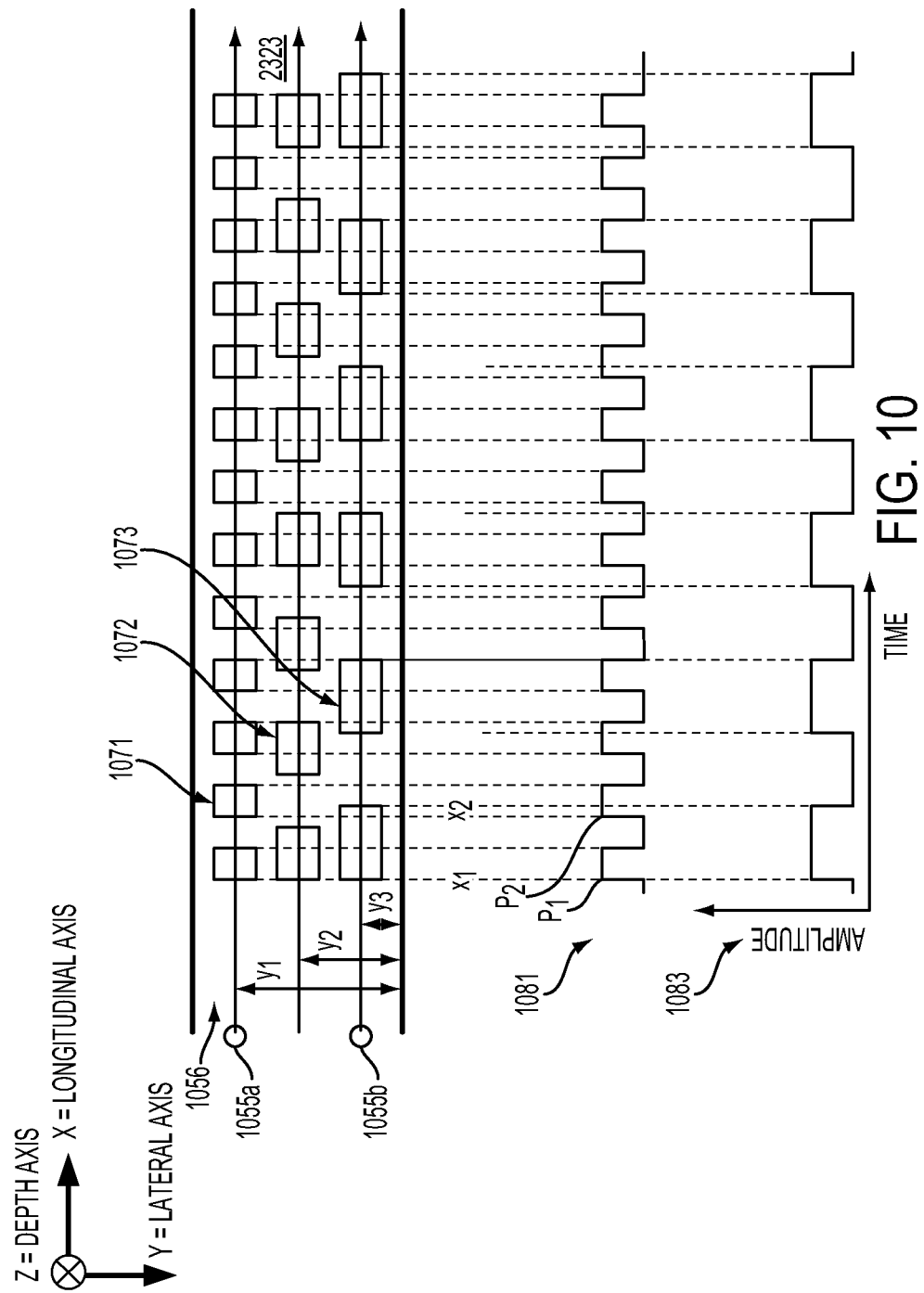
FIG. 10 is a plan view of another spatial filter disposed in the x-y plane and having mask features patterned according to another example embodiment to allow for determination of a lateral position and depth position of an object within the flow path.

FIG. 10 illustrates another type of spatial filter 1056 having mask features 1071, 1072, 1073 that change in frequency with respect to the lateral axis. Features 1071 are disposed along the longitudinal axis of the spatial filter at a first frequency, $f_1$, and at first constant lateral position, $y_1$. Features 1072 are disposed along the longitudinal axis of the spatial filter at a second frequency, $f_2$, and at second constant lateral position, $y_2$. Features 1073 are disposed along the longitudinal axis of the spatial filter at a third frequency, $f_3$, and at third constant lateral position, $y_3$, where $f_1 > f_2 > f_3$, and $y_1 > y_2 > y_3$.

The lower portion of FIG. 10 depicts detector output signals 1081, 1083 that are generated as light emanating from objects 1055a, 1055b interacts with mask features 1071, 1073. As shown in FIG. 10, the frequency of signal 1081 is greater than that of 1083. The frequency of the detector output signal can be used to determine lateral position of the objects. For example, signals 1081 having frequency $f_1$ are generated by objects 1055a flowing at a lateral position in the region of mask features 1071, e.g., $y_1 \pm \frac{1}{2}$ the width of the features 1071, where feature width is measured along the y axis. Signals 1082 having frequency $f_2$ are generated by objects 1055b flowing at a lateral position in the region of mask features 1072, e.g., $y_2 \pm \frac{1}{2}$ the width of the features 1072, wherein feature width is measured along the y axis. Thus, the frequency of the detector output signal can be used to determine lateral position of the object. Note that the objects 1055a, 1055b would not necessarily be flowing along the flow path at the same time as shown in FIG. 10, but both signals 1081, 1083 are shown along the same time axis for comparison of their respective signals.

Additionally, the trajectory depth in the flow channel of the object can be determined from the interaction of light emanating from particles 1055a, 1055b with mask features 1071, 1072, 1073 based on the amount of offset of the troughs (i.e., the lower modulation function) of the detector output signal, as previously discussed in connection with FIGS. 5-8. Furthermore, the longitudinal position of the objects can be determined based on the pulse number in the output signal. For example, considering object 1055a, the first output pulse, $P_1$, at frequency $f_1$ is associated with longitudinal position $x_1$, the second output pulse, $P_2$, at frequency $f_2$ is associated with longitudinal position $x_2$, and so forth. Thus, detector output signals generated by the interaction of light emanating from objects 1055a, 1055b interacting with spatial filter 1056 can be used to determine position of the objects in three dimensions. For the embodiments shown in FIGS. 9-10, the depth axis is along the detection axis of the detector.

Figure 11A:
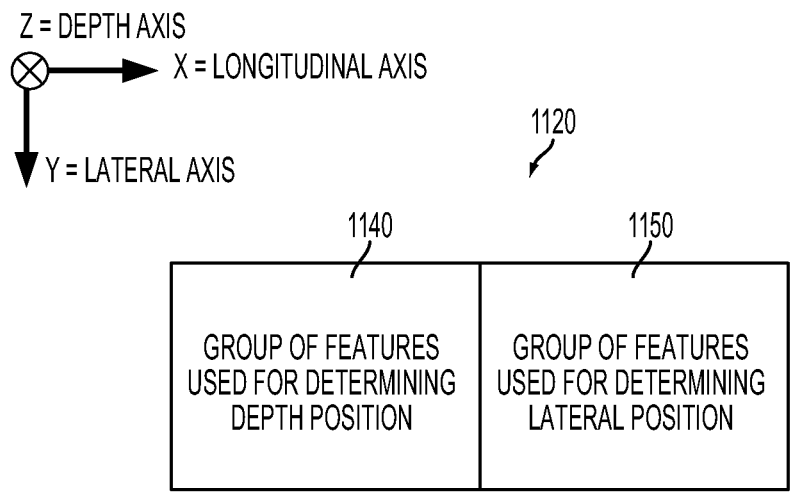
FIGS. 11A and 11B illustrate spatial filters that include first and second features wherein the first features are used to determine lateral position and the second features are used to determine depth position of an object.
Figure 11B:
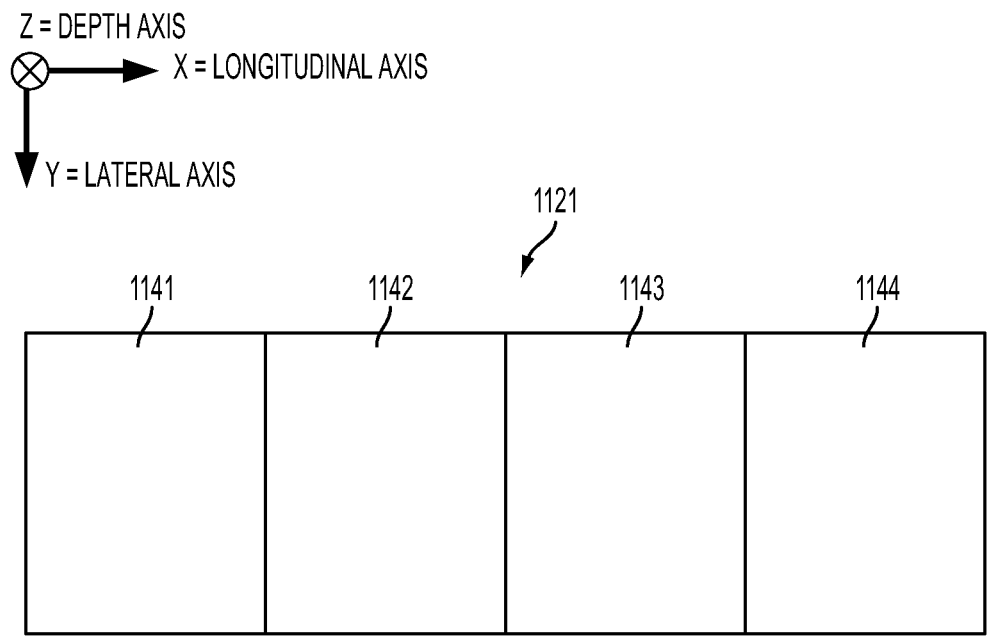

In some embodiments, two or more types of mask features may be used to determine the position of an object in multiple dimensions, e.g., along longitudinal, lateral, and trajectory depth axes. FIG. 11A illustrates a spatial filter 1120 that includes first and second regions 1140, 1150, wherein a first group of spatial features useful for determining depth position are arranged placed within the first region 1140 and group of spatial features useful for determining lateral position are arranged placed within the second region 1150. In some embodiments, the first group of features is useful for determining lateral position and the second group of features is useful for determining depth position. In some embodiments, as illustrated in FIG. 11B, the spatial filter 1121 includes more than two regions, wherein different groups of spatial features may be placed in the regions. For example, the first group of spatial features used to determine the trajectory depth position may be placed in regions 1141 and 1142 and the second group of spatial features used to determine lateral position can be disposed in regions 1143 and 1144. The features in all regions 1140, 1150, 1141, 1142, 1143, 1144 may be used to determine longitudinal position in some embodiments.

FIGS. 12-15 illustrate spatial filters that are useful for determining lateral position of an object in the flow path. These features useful for determining lateral position may be used in conjunction with additional features (not shown in FIGS. 12-15) of the spatial filter to determine trajectory depth position, as discussed in connection with the spatial filters of FIGS. 11A and 11B.

Figure 12:
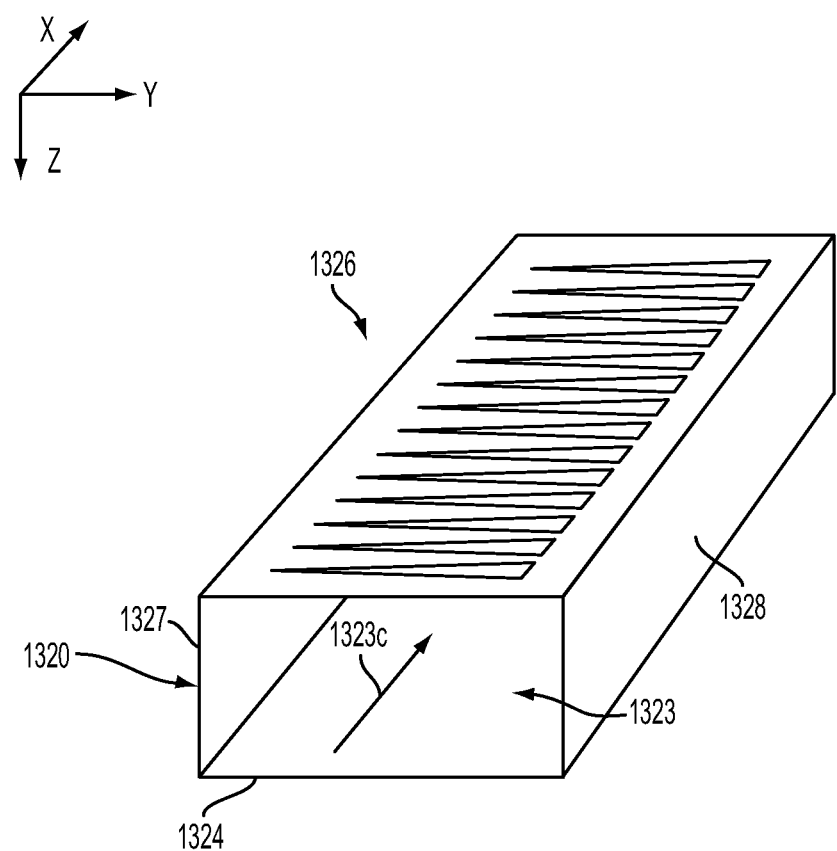
FIG. 12 is a perspective view of another spatial filter disposed in the x-y plane and having mask features patterned as transmissive triangles according to an example embodiment to allow for determination of a lateral position of an object within the flow path.

FIG. 12 shows a perspective view of a portion of a fluidic device 1320 and an embodiment of a spatial filter 1326. The fluidic device 1320 includes a flow path 1323 having a flow direction 1323c, and confining members 1324, 1327, and 1328. The confining members 1324, 1327, and 1328 are positioned to define the flow path 1323. The flow direction 1323c aligns generally with the x-direction of the Cartesian coordinate system illustrated in FIG. 12. In the embodiment shown, the spatial filter 1326 is mounted along a confining member (not shown) that extends generally along the x-y plane. In other embodiments, the spatial filter 1326 may be disposed externally to or within the flow channel 1323, and/or positioned relative to any of the other illustrated confining members 1324, 1327, and 1328. A detector may be positioned in any appropriate location to sense modulated light passing through the filter 1326. The detector is positioned so that it is capable of detecting light having a component that lies along the detection axis (i.e., the z-axis). In the illustrated embodiments, the detection axis is selected to be the depth axis.

For example, for a fluidic device 1320 and spatial filter 1326 having the orientation of FIG. 12, an excitation light source (also not shown in FIG. 12) can be oriented below confining member 1324 and a detector (not shown in FIG. 12) can be oriented above the filter 1326. In such an arrangement, excitation light from the light source passes through confining member 1324 and optically interacts with objects traveling within a detection region of the flow path 1323. The excitation light causes the objects to emanate light in all directions and a portion of the emanating light from the objects is spatially modulated by filter 1326. A detector positioned above the spatial filter senses the spatially modulated light and, in response, generates a time varying signal.

In FIG. 12, the spatial filter 1326 is arranged in the x-y plane of the Cartesian coordinate system. The spatial filter 1326 includes mask features that allow for a determination of a lateral position (i.e., a position in the y-direction of the Cartesian coordinate system) of an object within the flow path 1323. The spatial filter 1326 may also include mask features (not shown) that allow for determination of a trajectory depth position (i.e., a position in the z-direction of the Cartesian coordinate system) of an object within the flow path 1323. Each mask feature may be used to determine longitudinal position (i.e., a position in the x-direction of the Cartesian coordinate system) of an object within the flow path 1323.

Figure 13A:
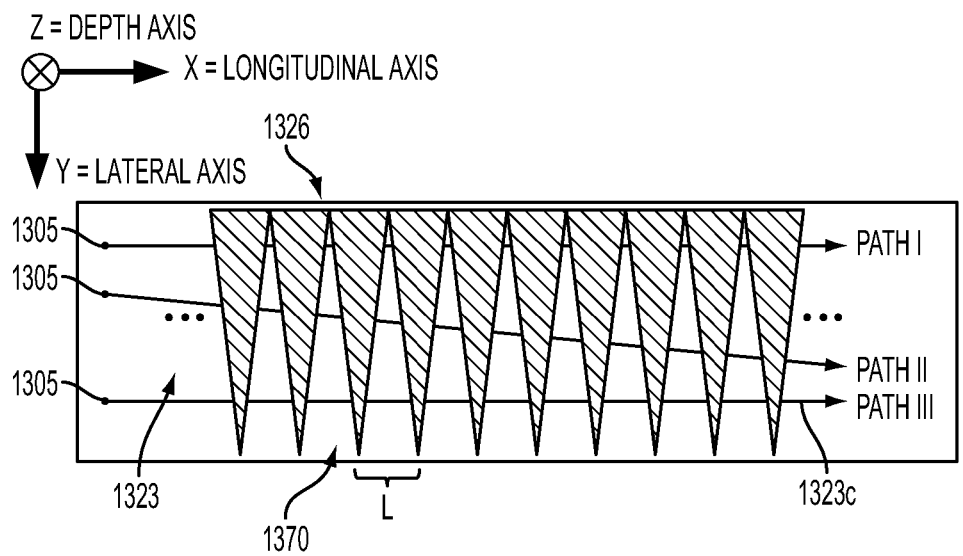
FIG. 13A is a plan view of the spatial filter of FIG. 12.

FIG. 13A shows a top plan view of the spatial filter 1326 of FIG. 12. The spatial filter 1326 has mask features 1370 that each have a length L with respect to a flow direction 1323c of the flow channel 1323, of a length that changes as each mask feature 1370 extends across the lateral axis y of the flow channel 1323. The mask features 1370 include transmissive and less transmissive regions and edges of some transmissive regions extend at a non-perpendicular angle with respect to the flow direction 1323c of the flow channel 1323. Although embodiments illustrated herein show triangular mask features, the mask features could alternatively be truncated triangles, parallelograms, or any other shape that has an edge that varies non-perpendicularly with respect to the flow direction. FIG. 13A additionally shows objects 1305 with different trajectories of flow across the filter 1326 as connoted by paths I-III. As shown in FIG. 13A, the mask features 1370 are periodic with respect to the flow direction 1323c of the flow channel 1323 and duty cycle of the mask features 1370 changes along the lateral y-axis y of the flow channel 1323.

Figure 13B:
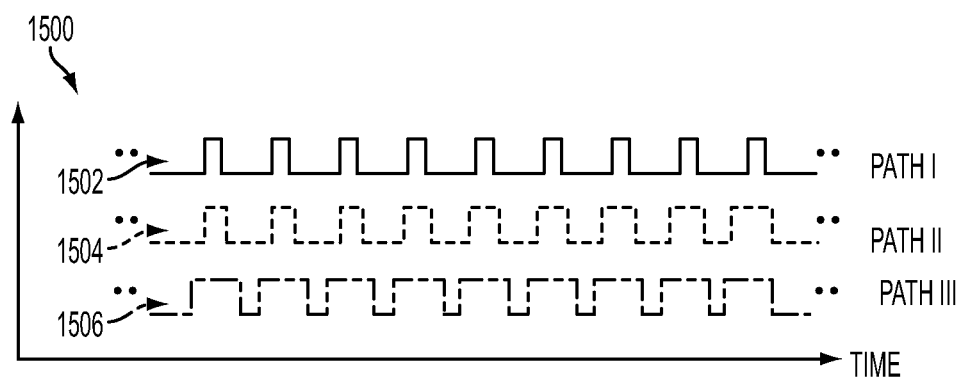
FIG. 13B is a plot that shows electrical signals that result from the three flow trajectories across the filter of FIG. 12.

FIG. 13B is a plot 1500 that shows detector output signals 1502, 1504, and 1506 that result from the objects 1305 flowing across the filter 1326 along paths I-III. In particular, signal 1502 corresponds with path I, signal 1504 corresponds with path II, and signal 1506 corresponds with path III. As shown plot 1500, the characteristics of the signals 1502, 1504, and 1506 are correlated to the geometry of the mask features 1370 and correspond to the lateral location of the object 1305 (FIG. 13A) within the flow channel 1323. Thus, the signal 1502 of path I has a relatively small duration of non-zero amplitude due to the small length L of the transmissive regions 1370 along path I. The configuration of filter 1326 also allows for determination of the trajectory of the objects 1305 in the x-y plane based upon changes in the characteristics of the signals. For example, signal 1504 experiences an increased duration of the signal in a peak region as the object 1305 flows along the filter 1326 in the x and y directions. This increase results from a gradually increasing length L (in the x direction) of the transmissive regions 1370 along path II, in addition to a small increase from the lateral shift (in y direction).

FIG. 14 shows a perspective view of a portion of a fluidic device 1620 and an embodiment of a spatial filter 1626. The fluidic device 1620 includes a flow path 1623 having a flow direction 1623c, and confining members 1624, 1627, and 1628. The confining members 1624, 1627, and 1628 are shown in the illustrated embodiment as being positioned to define the flow path 1623, but in other embodiments the confining members may not be present. The flow direction 1623c aligns generally with the x-direction of the Cartesian coordinate system illustrated in FIG. 14. In the embodiment shown, the spatial filter 1626 is mounted along a confining member (not shown) that extends generally along the x-y plane. In other embodiments, the spatial filter 1626 may be disposed externally to or within the flow channel 1623, and/or positioned relative to any of the illustrated confining members 1624, 1627, and 1628. A detector or multiple detectors (not shown) may be positioned in any appropriate location to sense modulated light passing through the filter 1626. In FIG. 14, the spatial filter 1626 has mask features that allow for a determination of a lateral position (i.e., a position in the y-direction of the Cartesian coordinate system) of an object within the flow channel 1623.

In some embodiments, the spatial filter may include the mask features as shown in spatial filter 1626 and may also include other mask features (not shown) that allow for determination of a trajectory depth position (i.e., a position in the z-direction of the Cartesian coordinate system) of an object within the flow path 1623. Each mask feature may be used to determine longitudinal position (i.e., a position in the x-direction of the Cartesian coordinate system) of an object within the flow path 1623.

Figure 15A:
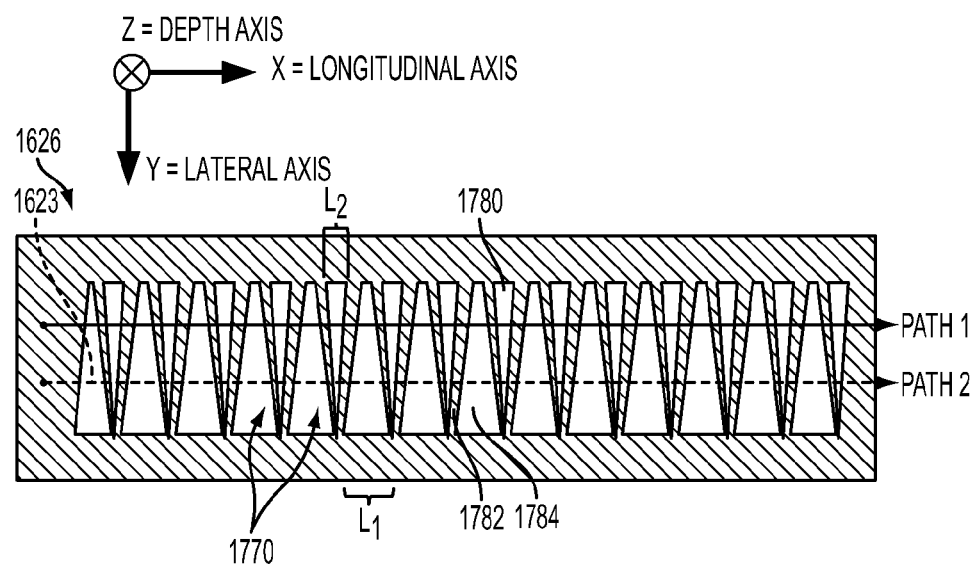
FIG. 15A is a plan view of the spatial filter of FIG. 14.

FIG. 15A shows a side plan view of the spatial filter 1626 of FIG. 14. The spatial filter 1626 has mask features 1770 with two alternating sizes and orientations. In the exemplary embodiment, first transmissive mask features 1784 are separated from second transmissive mask features 1780 by less-transmissive mask features 1782 in a pattern of interdigitated triangles. In one embodiment, the first mask features 1784 comprise first triangles, e.g., isosceles triangles, with a first angle and second mask features 1780 comprise second triangles, e.g., isosceles triangles, with a second angle that differs from the first angle. The first mask features 1784 have a length $L_1$ with respect to the longitudinal x-axis that changes as each first mask feature 1784 extends along the lateral y axis of the flow channel 1723. Additionally, the second mask features 1780 have a length $L_2$ with respect to the longitudinal x-axis that changes as each second mask feature 1780 extends along the lateral y axis. FIG. 15A additionally shows objects 1305a, 1305b traveling at two different trajectories of flow across the filter 1626 at differing lateral positions 1306a, 1306b.

Figure 15B:
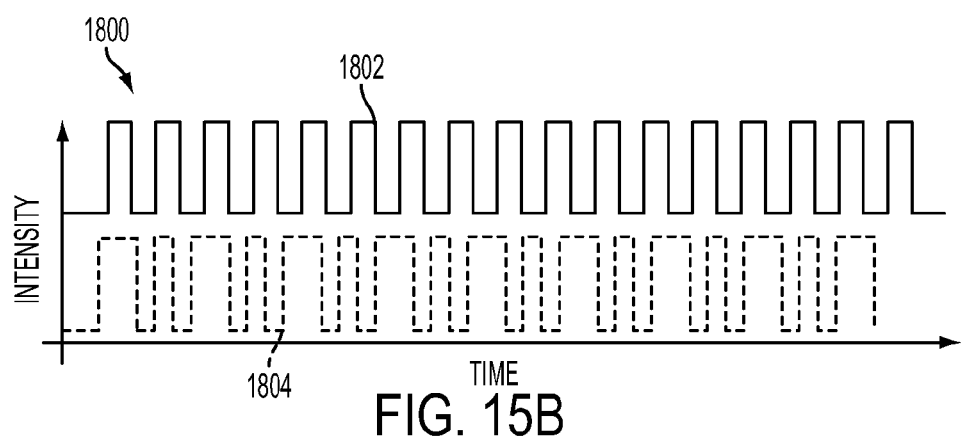
FIG. 15B is a plot that shows electrical signals that result from the two flow trajectories across the filter of FIG. 14.

FIG. 15B is a plot 1800 that shows detector output signals 1802 and 1804 that result from objects flowing across the filter 1626 along paths (PATH 1, PATH II) at different lateral positions. In particular, signal 1802 corresponds to an object traveling along PATH I where $L_1 \approx L_2$ for first transmissive mask feature 1784 and second transmissive mask features 1780. Signal 1804 corresponds to an object traveling along PATH II where $L_1 > L_2$. As shown in plot 1800, the characteristics of the signals 1802 and 1804 are correlated to the geometry of the mask features 1770 and correspond to the lateral position of the objects. For example, the detector output signal generated for an object traveling along a trajectory where $L_1 \approx L_2$ has a single predominant frequency component. The detector output signal generated for an object traveling along a trajectory where $L_1$ is different from $L_2$ has two predominant frequency components. Thus, the lateral position of the object can be determined using a Fourier transform to convert the signal to the frequency domain and then analyzing the intensity peaks of the transformed signal to determine the predominant frequency components. These frequency components map to a lateral position of the flow path. The configuration of filter 1726 also allows for determination of the position and/or trajectory of the objects in the x-y plane based upon changes in the characteristics of the signals.

Spatial masks that are useful for determining lateral position of objects are illustrated in FIGS. 12-15 as having patterns of triangular features. It will be appreciated mask features other than triangular features can be used in various embodiments. Using spatial filters to modulate light as described herein, the position of an object in a flow path can be determined using a spatial filter that has mask features with a changing characteristic such as an edge between first and second mask features having a non-perpendicular and non-parallel orientation with respect to the flow direction along the trajectory depth direction of the flow channel. The changing characteristic causes a change in at least one of the duty cycle, frequency, or phase in the time-varying signal generated by the detector. In many applications it may be useful to determine the velocity of the objects. Object velocity can be determined by determining the frequency of the transitions in the time varying output signal and/or by transforming the time varying signal to a frequency domain signal and analyzing the dominant frequencies having the largest amplitude.

Some systems are capable of determining the position of an object in three dimensions. In some embodiments, systems that determine a three dimensional position of objects use two (or more) masks oriented in different planes. For example a first mask that includes a first group of mask features may be used for detecting lateral position and a second mask includes a second group of mask features may be used for detecting depth position. In such a system, a first detector is arranged relative to the first mask so that the first detector detects light emanating from objects flowing along a flow path that is spatially modulated by the first mask. The first detector generates a first output signal in response to the emanating light that is spatially modulated by the first mask. A second detector is oriented relative to the second mask so that the second detector detects light emanating from objects flowing along a flow path that is spatially modulated by the second mask.

Figure 16:
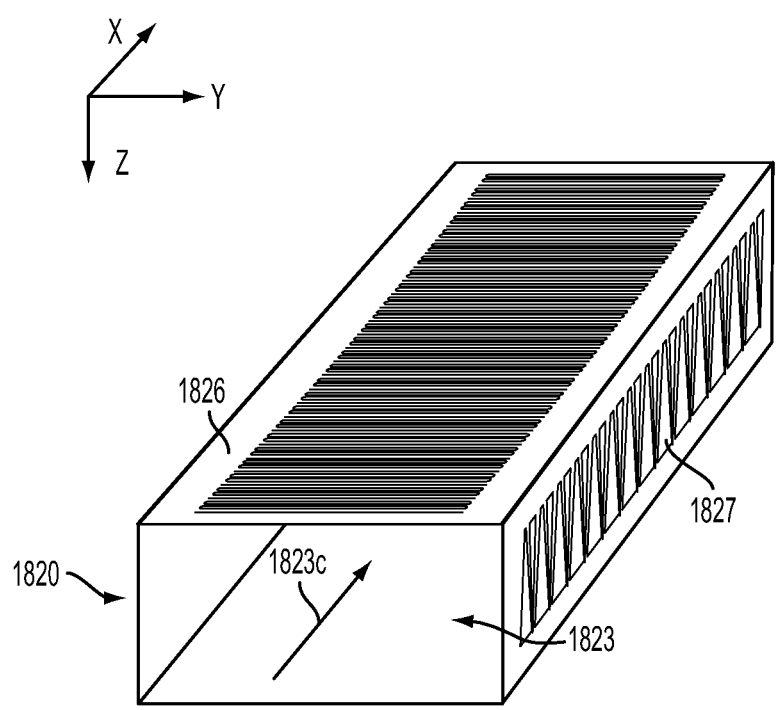
FIG. 16 shows a perspective view of a portion of a fluidic device and two spatial filters in accordance with some embodiments.

FIG. 16 shows a perspective view of a portion of a fluidic device 1820 and two spatial filters. A first spatial filter 1826 is oriented with respect to the flow path 1823 extending generally in the x-y plane and a second spatial filter 1827 is oriented with respect to a flow path 1823 extending generally in the x-z plane. The flow direction 1823c aligns generally with the longitudinal x-direction of the Cartesian coordinate system illustrated in FIG. 16.

The spatial filter 1826 has a first group of mask features that allow for a determination of a depth position (i.e., a position in the z-direction of the Cartesian coordinate system) of an object within the flow channel 1823. The spatial filter 1827 includes a second group of mask features that allow for a determination of a lateral position (i.e., a position in the y-direction of the Cartesian coordinate system) of an object within the flow channel 1823. Either or both groups of mask features may be used to determine longitudinal position (i.e., a position in the x-direction of the Cartesian coordinate system) of an object within the flow channel 1823.

Figure 17:
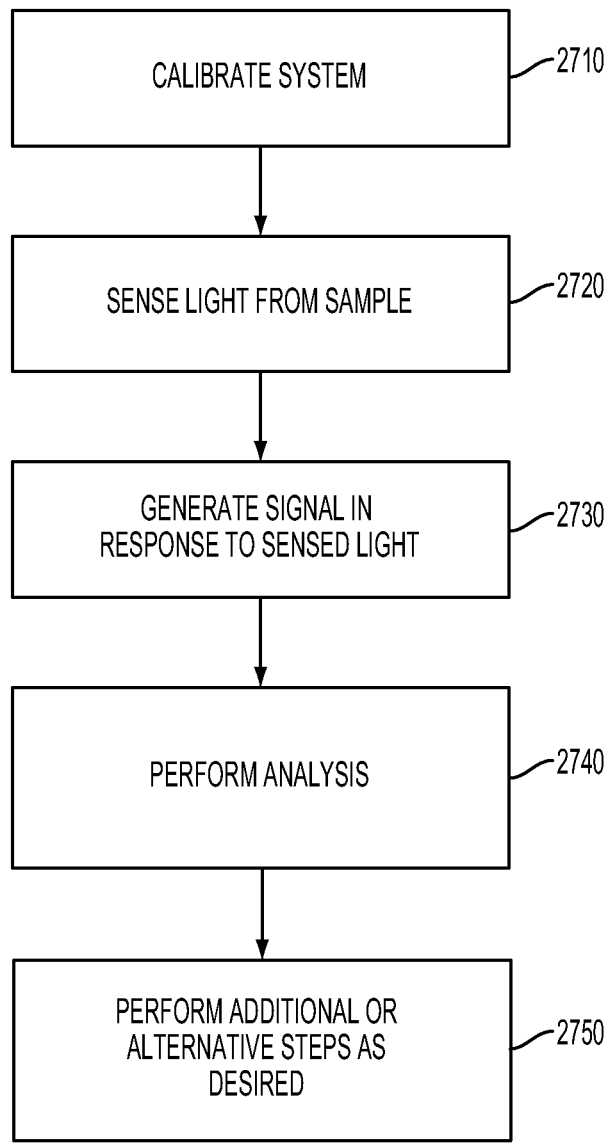
FIG. 17 is a flow diagram of a method of determining object position according to an example embodiment.

FIG. 17 shows a flow diagram of a method of analyzing a sample. As part of an initialization 2710 for the system, objects of a known size and/or luminescence are passed through a flow path relative to a spatial filter at different depths and/or lateral positions so that the system can be calibrated. The primary purpose of the calibration step is to perform a system validation to verify that the system is tuned properly, to ensure that all the parameters are set properly, and that the system can correctly identify the type of objects and successfully determine their position, velocity and depth trajectory as the case may be. For example, prior to running the actual sample to be measured, and subsequently in frequent time intervals thereafter, a pre-made mixture of certain object sizes is applied through the flow channel to verify that the system can correctly determine their position, velocity and trajectory depth in the flow channel. The objects may additionally be coated with different materials to simulate for example different intensity levels and/or other system aspects. If the system is found to drift over time away from the known object dimensions, the system parameters can be tuned to compensate and bring it back to within accuracy specification. The calibration step is optional. The system information may also be gathered over time during regular use of the system by applying a machine learning algorithm.

Light from the sample containing an object of interest is sensed 2720 as the object moves through the flow path relative to the spatial filter. As discussed previously, the sensed light is modulated according to mask features. An electrical output signal is generated 2730 in response to the sensed light. The signal is analyzed 2740 to determine at least a trajectory depth of the object within the flow path. Additional steps 2750 and/or alternative steps can be performed as desired to support the method described.

Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

What is claimed is:

1. An assembly, comprising:
   at least one spatial filter having a length along a longitudinal axis of a flow path and a width along a lateral axis of the flow path, the spatial filter having mask features disposed at least partially along the length of the spatial filter and extending at least partially across the width of the spatial filter, the mask features including at least first mask features having a first transmission characteristic and second mask features having a second transmission characteristic different from the first transmission characteristic;
   at least one detector positioned to detect light with respect to a detection axis, the detection axis making a non-zero angle with respect to the longitudinal and lateral axes, the detected light emanating from at least one object and modulated according to the mask features as the object moves along the longitudinal axis, the detector configured to generate a time-varying electrical signal in response to the detected light, the time-varying electrical signal including information about a depth of the object in the flow path along the detection axis, the information contained in at least one of an amplitude and a morphology characteristic of the time-varying electrical signal, the characteristic being variable with respect to the depth axis; and
   an analyzer configured to determine the depth of the object based on the information in the time-varying electrical signal.

2. The assembly of claim 1, wherein:
   the spatial filter is positioned between a light source that provides measurement light and the object; and
   the spatial filter interacts with the measurement light to provide spatially modulated measurement light.

3. The assembly of claim 1, wherein:
   the spatial filter is positioned between the object and the detector; and
   the light emanating from the object interacts with the spatial filter to provide modulation of the sensed light.

4. The assembly of claim 1, wherein:
   the light emanating from the object interacts with the spatial filter to provide cones of light that emerge from the mask, the angle of each cone related to the depth of the object;
   the time-varying signal includes at least one characteristic associated with the angle of the cone; and
   the analyzer is configured to determine the depth of the object based on the characteristic in the time-varying signal associated with the angle of the cone.

5. The assembly of claim 1, wherein:
   the first mask features alternate with the second mask features;
   the first mask features comprise at least two transmissive regions having length L1, each transmissive region of length L1 separated from another transmissive region of length L1 by a less-transmissive region of length L2, where L1>L2; and
   the second mask features comprise at least two less-transmissive regions having length L1, each less-transmissive region of length L1 separated from another less transmissive region of length L1 by a transmissive region of length L2.

6. The assembly of claim 1, wherein:
   the time-varying signal generated in response to the modulated light includes a first signal component of a first frequency superimposed with a second signal component of a second frequency, the first frequency being different from the second frequency.

7. The assembly of claim 6, wherein the second frequency is a multiple of the first frequency.

8. An assembly, comprising:
   at least one spatial filter having a length along a longitudinal axis of a flow path and a width along a lateral axis of the flow path, the spatial filter having mask features disposed at least partially along the length of the spatial filter and extending at least partially across the width of the spatial filter, the mask features including at least first mask features having a first transmission characteristic and second mask features having a second transmission characteristic different from the first transmission characteristic;
   at least one detector positioned to detect light with respect to a detection axis, the detection axis making a non-zero angle with respect to the longitudinal and lateral axes, the detected light emanating from at least one object and modulated according to the mask features as the object moves along the longitudinal axis, the detector configured to generate a time-varying electrical signal in response to the detected light, the time-varying electrical signal including information about a depth of the object in the flow path along the detection axis; and
   an analyzer configured to determine the depth of the object based on the signal;
   wherein the time-varying signal generated in response to the modulated light includes a first signal component of a first frequency superimposed with a second signal component of a second frequency, the first frequency being different from the second frequency; and the analyzer is configured to determine the depth of the object in the flow channel by comparing the amplitude of the first signal component to the amplitude of the second signal component.

9. The assembly of claim 1, wherein:
   the time-varying signal generated in response to the modulated light includes a first signal component of a first frequency superimposed with a second signal component of a second frequency, the first frequency being different from the second frequency; and
   the analyzer is configured to perform a Fourier transform of the time-varying signal and to compare an amplitude of the Fourier transform signal at the first frequency to an amplitude of the Fourier transform signal at the second frequency to determine the depth position of the object.

10. The assembly of claim 9, wherein the analyzer is configured to determine the depth of the object in the flow channel based on a difference between the amplitude of the Fourier transform signal at the first frequency and the amplitude of the Fourier transform signal at the second signal component.

11. An assembly, comprising:
at least one spatial filter having a length along a longitudinal axis of a flow path and a width along a lateral axis of the flow path, the spatial filter having mask features disposed at least partially along the length of the spatial filter and extending at least partially across the width of the spatial filter, the mask features including at least first mask features having a first transmission characteristic and second mask features having a second transmission characteristic different from the first transmission characteristic;
at least one detector positioned to detect light with respect to a detection axis, the detection axis making a non-zero angle with respect to the longitudinal and lateral axes, the detected light emanating from at least one object and modulated according to the mask features as the object moves along the longitudinal axis, the detector configured to generate a time-varying electrical signal in response to the detected light, the time-varying electrical signal including information about a depth of the object in the flow path along the detection axis; and
an analyzer configured to determine the depth of the object based on the signal wherein:
the signal generated in response to the sensed light has a modulation envelope, the modulation envelop defined by a lower envelope function and an upper envelope function; and
the analyzer is configured to determine the depth of the object based on one or more characteristics of the modulation envelope.

12. The assembly of claim 11, wherein the depth is determined based on an amount of modulation of the lower envelope function.

13. The assembly of claim 1, wherein:
an edge between the first and second mask features for at least some of the mask features extends at an angle that is not perpendicular and not parallel to the longitudinal axis of the mask; and
the spatial filter includes at least one reference feature that is substantially parallel to the lateral axis.

14. The assembly of claim 13, wherein the time-varying signal also includes information about a position of the object along at least one of the lateral and longitudinal axes.

15. The assembly of claim 1, wherein:
the first mask features alternate with the second mask features;
the first mask features comprise at least two transmissive regions having length L1, each transmissive region of length L1 separated from another transmissive region of length L1 by a less transmissive region of length L2, where L1>L2; and
the second mask features comprise at least two less-transmissive regions having length L1, each less-transmissive region of length L1 separated from another less transmissive region of length L1 by a transmissive region of length L2, wherein each mask feature has at least one edge that is not parallel and not perpendicular to the longitudinal axis of the mask.

16. The assembly of claim 1, wherein the mask features have a changing frequency across the lateral axis of the spatial filter.

17. The assembly of claim 1, wherein the analyzer is further configured to determine position of the object along the lateral and longitudinal axes based on the signal.

18. The assembly of claim 1, wherein:
the spatial filter includes:
a first set of first and second mask features; and
second set of first and second mask features;
the detector is configured to generate a time varying electrical signal, the time varying electrical signal having a first portion generated in response to detected light modulated according to the first set of mask features and having a second portion generated in response to detected light modulated according to the second set of mask features.

19. The assembly of claim 18, wherein at least one edge between a first mask feature and a second mask feature of the first set of mask features is not parallel or perpendicular to the longitudinal axis.

20. The assembly of claim 19, wherein the first set of mask features includes one or more triangular mask features.

21. An assembly, comprising:
a first spatial filter arranged along an x-y plane of a flow path characterized in three dimensional space by x, y, and z axes, the first spatial filter having a first group of mask features;
a second spatial filter arranged along an x-z plane of the flow path, the second spatial filter having a second group of mask features;
a first detector positioned to detect light emanating from at least one object and modulated according to the first group of mask features as the object moves along the flow path, the first detector configured to generate a first time-varying electrical signal in response to the detected light modulated according to the first group of mask features;
a second detector positioned to detect light emanating from at least one object and modulated according to the second group of mask features as the object moves along the flow path, the second detector configured to generate a second time-varying electrical signal in response to the detected light modulated according to the second group of mask features; and
an analyzer configured to determine a position of the object along the x, y, and z axes based on the first and second time-varying signals.

22. The assembly of claim 21, wherein at least one edge between a first mask feature and a second mask feature of the first group of mask features is not parallel or perpendicular to a flow direction of the flow path.

23. A method, comprising:
detecting light emanating from objects moving along a flow path, the emanating light modulated by at least one spatial filter having a length along a longitudinal axis of a flow path and a width along a lateral axis of the flow path, the spatial filter having mask features configured to modulate light, the detected light having a component along a detection axis that makes a non-zero angle with respect to the longitudinal and lateral axes;
generating a time-varying electrical output signal in response to the detected light, the time-varying electrical output signal including information contained in at least one of an amplitude and a morphological characteristic of the time-varying electrical output signal that corresponds to the component of the detected light, the characteristic being variable with respect to the depth axis; and determining a depth of the object in the flow path along the detection axis based on the information in the time-varying electrical output signal.

24. The method of claim 23, wherein determining the depth of the object comprises performing a time domain analysis.

25. The method of claim 23, wherein determining the depth of the object comprises performing a frequency domain analysis.

26. The system of claim 1, wherein the amplitude characteristic comprises one or both of a peak maximum and a peak minimum of the signal.

27. The system of claim 1, wherein the morphology characteristic comprises one or both of a rise time and a fall time of the signal.

* * * * *